(12) United States Patent
Hodorek et al.

(10) Patent No.: US 8,876,830 B2
(45) Date of Patent: Nov. 4, 2014

(54) VIRTUAL IMPLANT PLACEMENT IN THE OR

(75) Inventors: Robert A. Hodorek, Warsaw, IN (US); Joel Zuhars, Warsaw, IN (US); Jody L. Claypool, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 379 days.

(21) Appl. No.: 12/854,610

(22) Filed: Aug. 11, 2010

(65) Prior Publication Data

US 2011/0196377 A1 Aug. 11, 2011

Related U.S. Application Data

(60) Provisional application No. 61/233,526, filed on Aug. 13, 2009, provisional application No. 61/317,959, filed on Mar. 26, 2010, provisional application No. 61/318,537, filed on Mar. 29, 2010.

(51) Int. Cl.
*A61B 17/58* (2006.01)
*A61B 17/15* (2006.01)
*A61B 19/00* (2006.01)

(52) U.S. Cl.
CPC ......... *A61B 17/155* (2013.01); *A61B 2019/508* (2013.01); *A61B 17/157* (2013.01); *A61B 19/5244* (2013.01); *A61B 2019/5483* (2013.01)
USPC .............................................. 606/87; 606/88

(58) Field of Classification Search
USPC ...................................................... 606/87–88
See application file for complete search history.

(56) References Cited

U.S. PATENT DOCUMENTS

| | | |
|---|---|---|
| 5,415,169 A | 5/1995 | Siczek et al. |
| 5,432,703 A | 7/1995 | Clynch et al. |
| 5,526,814 A | 6/1996 | Cline et al. |
| 5,769,078 A | 6/1998 | Kliegis |
| 6,124,843 A | 9/2000 | Kodama |
| 6,328,744 B1 | 12/2001 | Harari et al. |
| 6,402,782 B1 | 6/2002 | Sibbald et al. |
| 6,468,265 B1 | 10/2002 | Evans et al. |
| 6,499,488 B1 | 12/2002 | Hunter et al. |
| 6,545,664 B1 | 4/2003 | Kim |
| 6,554,837 B1 | 4/2003 | Hauri et al. |
| 6,591,581 B2 | 7/2003 | Schmieding |
| 6,610,067 B2 | 8/2003 | Tallarida et al. |
| 6,697,664 B2 | 2/2004 | Kienzle, III et al. |
| 6,843,796 B2 | 1/2005 | Harari et al. |
| 6,947,783 B2* | 9/2005 | Immerz ...................... 600/410 |
| 7,029,479 B2 | 4/2006 | Tallarida et al. |
| 7,050,845 B2 | 5/2006 | Vilsmeier |
| 7,203,277 B2 | 4/2007 | Birkenbach et al. |
| 7,314,048 B2 | 1/2008 | Couture et al. |
| 7,317,955 B2 | 1/2008 | McGreevy |

(Continued)

FOREIGN PATENT DOCUMENTS

| | | |
|---|---|---|
| EP | 1372516 | 9/2002 |
| EP | 1395194 | 12/2002 |

(Continued)

*Primary Examiner* — Nicholas Woodall
(74) *Attorney, Agent, or Firm* — Norton Rose Fulbright Canada LLP

(57) ABSTRACT

A virtual implant placement method and system comprising models of implants and/or bones linked to tracking assemblies mounted onto the bones. A joint model is constructed intraoperatively based on the positions of the tracking assemblies to determine the positions of cut planes.

38 Claims, 16 Drawing Sheets

(56) References Cited

U.S. PATENT DOCUMENTS

| | | |
|---|---|---|
| 7,366,561 B2 | 4/2008 | Mills et al. |
| 7,447,537 B1 | 11/2008 | Funda et al. |
| 7,470,244 B2 | 12/2008 | Harrison, Jr. |
| 7,520,800 B2 | 4/2009 | Duescher |
| 7,520,880 B2 | 4/2009 | Claypool et al. |
| 7,567,833 B2 | 7/2009 | Moctezuma de la Barrera et al. |
| 7,630,752 B2 | 12/2009 | Viswanathan |
| 7,704,254 B2 | 4/2010 | Walen |
| 7,715,602 B2 | 5/2010 | Richard |
| 2002/0010465 A1 | 1/2002 | Koo et al. |
| 2003/0060808 A1 | 3/2003 | Wilk |
| 2003/0078003 A1 | 4/2003 | Hunter et al. |
| 2004/0172044 A1 | 9/2004 | Grimm et al. |
| 2004/0236342 A1 | 11/2004 | Ferree et al. |
| 2005/0149041 A1 | 7/2005 | McGinley et al. |
| 2005/0162380 A1 | 7/2005 | Paikattu et al. |
| 2005/0171553 A1 | 8/2005 | Schwarz et al. |
| 2005/0261699 A1 | 11/2005 | Neubauer et al. |
| 2006/0173269 A1 | 8/2006 | Glossop |
| 2006/0200158 A1 | 9/2006 | Farling et al. |
| 2006/0247647 A1 | 11/2006 | Hodorek et al. |
| 2006/0271056 A1 | 11/2006 | Terrill-Grisoni et al. |
| 2006/0293681 A1 | 12/2006 | Claypool et al. |
| 2007/0005073 A1 | 1/2007 | Claypool et al. |
| 2007/0015999 A1 | 1/2007 | Heldreth et al. |
| 2007/0016008 A1 | 1/2007 | Schoenefeld |
| 2007/0038223 A1 | 2/2007 | Marquart et al. |
| 2007/0121065 A1 | 5/2007 | Cox et al. |
| 2007/0156066 A1 | 7/2007 | McGinley et al. |
| 2007/0213692 A1 | 9/2007 | Neubauer et al. |
| 2007/0219560 A1 | 9/2007 | Hodorek et al. |
| 2007/0239153 A1 | 10/2007 | Hodorek et al. |
| 2007/0255288 A1* | 11/2007 | Mahfouz et al. ............ 606/102 |
| 2008/0015677 A1 | 1/2008 | Glossop et al. |
| 2008/0051677 A1 | 2/2008 | Bharadwaj |
| 2008/0058947 A1 | 3/2008 | Earl et al. |
| 2008/0065082 A1 | 3/2008 | Chang et al. |
| 2008/0065085 A1 | 3/2008 | Couture et al. |
| 2008/0065098 A1 | 3/2008 | Larkin |
| 2008/0097616 A1 | 4/2008 | Meyers et al. |
| 2008/0103509 A1 | 5/2008 | Goldbach |
| 2008/0108912 A1* | 5/2008 | Node-Langlois ............. 600/587 |
| 2008/0119724 A1 | 5/2008 | Williamson |
| 2008/0119860 A1 | 5/2008 | McCarthy |
| 2008/0140081 A1 | 6/2008 | Heavener et al. |
| 2008/0154274 A1 | 6/2008 | Claypool et al. |
| 2008/0161824 A1 | 7/2008 | McMillen |
| 2008/0188942 A1 | 8/2008 | Brown et al. |
| 2008/0221680 A1 | 9/2008 | Hodorek |
| 2008/0306484 A1 | 12/2008 | Coon et al. |
| 2008/0306485 A1 | 12/2008 | Coon et al. |
| 2008/0312529 A1 | 12/2008 | Amiot et al. |
| 2009/0062804 A1 | 3/2009 | Runquist et al. |
| 2009/0088674 A1* | 4/2009 | Caillouette et al. ............ 602/26 |
| 2009/0112213 A1 | 4/2009 | Heavener et al. |
| 2009/0138019 A1 | 5/2009 | Wasielewski |
| 2009/0143670 A1 | 6/2009 | Daigneault |
| 2009/0163808 A1 | 6/2009 | Peyrard et al. |
| 2009/0163809 A1 | 6/2009 | Kane et al. |
| 2009/0182226 A1 | 7/2009 | Weitzner et al. |
| 2009/0192722 A1* | 7/2009 | Shariati et al. ................. 702/19 |
| 2009/0203989 A1 | 8/2009 | Burnside et al. |
| 2009/0209851 A1 | 8/2009 | Blau |
| 2009/0221908 A1 | 9/2009 | Glossop |
| 2009/0299477 A1 | 12/2009 | Clayton et al. |
| 2010/0049148 A1 | 2/2010 | Siniaguine |
| 2010/0063523 A1 | 3/2010 | Menard et al. |
| 2010/0100081 A1 | 4/2010 | Tuma et al. |
| 2010/0137881 A1 | 6/2010 | Kamer |
| 2010/0137882 A1 | 6/2010 | Quaid, III |

FOREIGN PATENT DOCUMENTS

| | | | |
|---|---|---|---|
| EP | 1444957 | A1 | 8/2004 |
| WO | WO2004/016178 | A2 | 2/2004 |
| WO | WO2005/009215 | A2 | 2/2005 |
| WO | WO2005/048852 | A1 | 6/2005 |
| WO | WO2009/061825 | A1 | 5/2009 |
| WO | WO2009/094646 | A2 | 7/2009 |
| WO | WO2009/105479 | A1 | 8/2009 |
| WO | WO2010/046455 | | 4/2010 |
| WO | WO2010/047703 | A2 | 4/2010 |

* cited by examiner

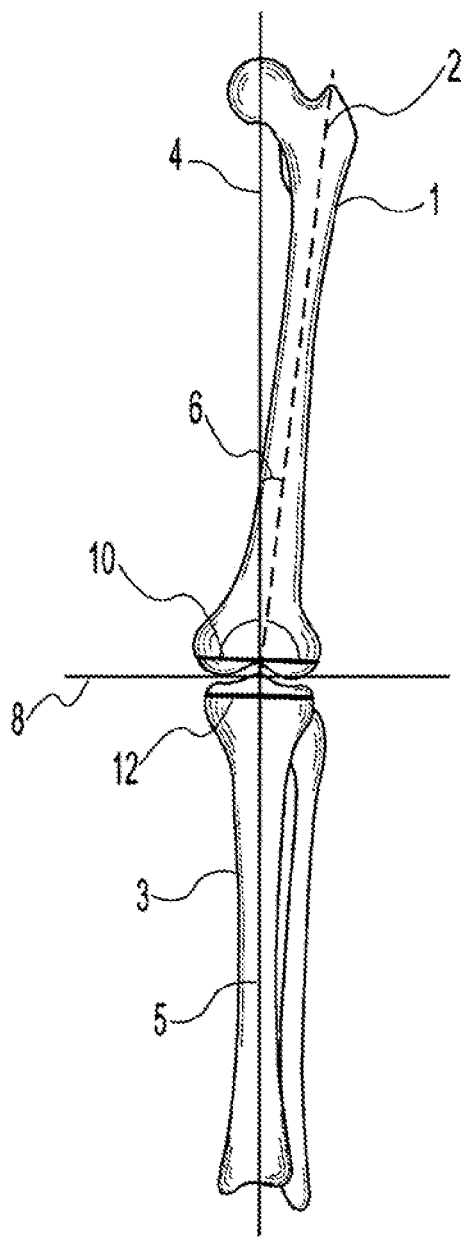
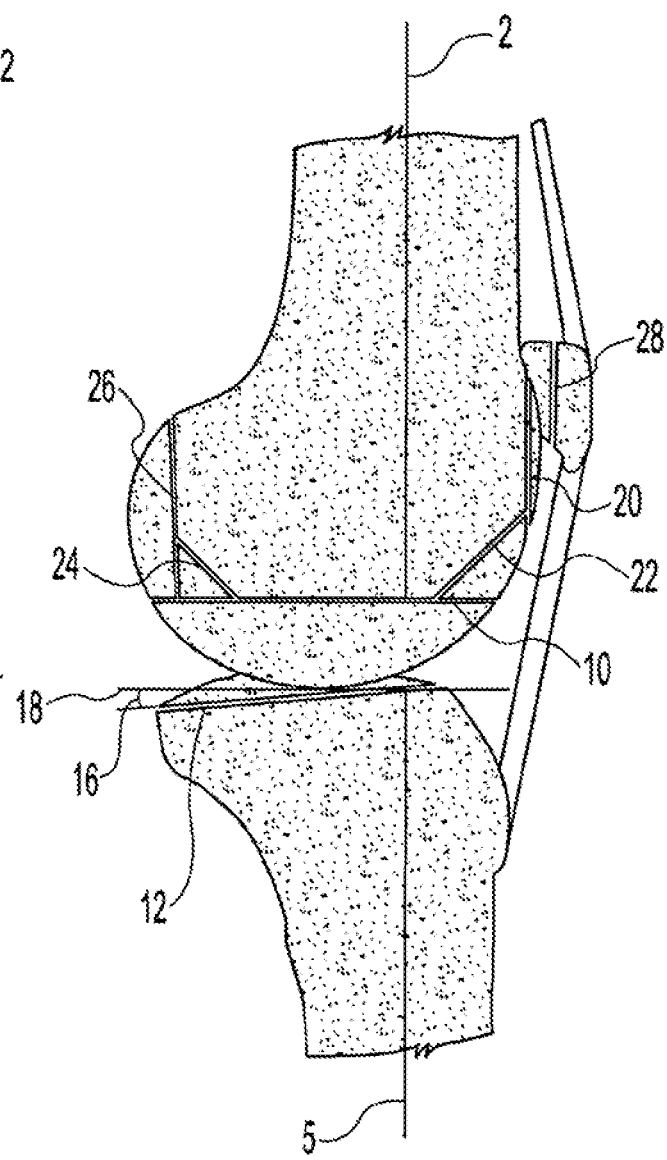
FIG. 1
FIG. 2

VIRTUAL IMPLANT PLACEMENT IN THE OR

CROSS-REFERENCE TO RELATED APPLICATIONS

This application claims the benefit of priority from U.S. Patent Application Ser. No. 61/233,526 entitled VIRTUAL IMPLANT PLACEMENT IN THE OR filed on Aug. 13, 2009, U.S. Patent Application Ser. No. 61/317,959 entitled COMPACT COMPUTER ASSISTED SURGICAL SYSTEM filed on Mar. 26, 2010, and U.S. Patent Application Ser. No. 61/318,537 entitled AUTOMATICALLY STABILIZED BONE RESECTION TOOL filed on Mar. 29, 2010, the disclosures of which are expressly incorporated by reference herein in their entirety.

FIELD OF THE DISCLOSURE

The present disclosure relates generally to a system and method for resectioning at least one bone. More particularly, the present invention relates to a system comprising digital models and a resectioning method using the models.

BACKGROUND

Degenerative and/or traumatic damage to skeletal joints or other locations within a patient's body may require surgical intervention. During such surgical intervention, it is often necessary to position and/or support a surgical component at a desired location relative to the surgical site. Surgical components may include implants, trial implants, drills, burrs, saws, lasers, thermal ablators, electrical ablators, retractors, clamps, cameras, microscopes, guides, and other surgical components. Surgical sites may include a hip joint, knee joint, vertebral joint, shoulder joint, elbow joint, ankle joint, digital joint of the hand or foot, jaw, fracture site, tumor site, and other suitable surgical sites. For example, damage to the articular cartilage of a skeletal joint can result in pain and restricted motion. Prosthetic joint replacement is frequently utilized to alleviate the pain and restore joint function. In this procedure, the damaged parts of the joint are cut away and replaced with prosthetic components. Typically a resection guide is used to guide a cutter such as a saw blade or burr to cut a desired portion of the bone to prepare a seating surface for a prosthetic component. The resection guide must be carefully positioned to guide the cut at the appropriate location.

Many surgical procedures are now performed with surgical navigation systems in which sensors detect tracking elements attached in known fixed relationship to objects in the surgical environment such as surgical instruments, implants, or patient body parts. The sensors information is transmitted to a computer that triangulates the position and orientation of the tracking elements within surgical navigation system coordinates. Thus, based on the fixed relationship between the objects and the tracking elements, the computer can resolve the position and orientation of the objects and provide position and orientation feedback for surgeon guidance.

An anatomical joint formed between two bones comprises three planes and three rotation axes relative to the joint line and each bone with respect to the other. In a knee joint, the planes are known as the medial/lateral, anterior/posterior, and proximal/distal planes while the rotation axes are known as the external rotation of the femur, extension plane rotation, and varus/valgus rotation. FIG. 1 illustrates a femur 1, a tibia 3, and various axes of the knee joint in the frontal plane. Femur 1 has an anatomic axis 2 coinciding generally with its intramedullary canal. It also has a mechanical axis 4, or load axis, running from the center of the femoral head to the center of the knee. An angle 6 between axes 2, 4 in the frontal plane varies within the patient population but is on the order of 4-9°. Axes 2, 4 are approximately superimposed in the sagittal plane (FIG. 2). Likewise, tibia 3 has a mechanical axis 5 coinciding generally with its intramedullary canal. Mechanical axis 5 of the tibia runs from the center of the knee to the center of the ankle. The knee flexes about a joint line 8.

FIG. 2 illustrates the knee joint from the side or sagittal view and various bone cuts that may be made to align implant components. A distal femoral cut 10 is typically made perpendicular to femoral axes 2, 4 in the sagittal plane. A proximal tibial resection 12 is typically cut to match the natural posterior slope, or rotation, 16 of the proximal tibia relative to mechanical axes 4, 5 and an axis 18 which is perpendicular to mechanical axis 5. The distance between distal femoral cut 10 and proximal tibial cut 12 along mechanical axes 4, 5 is the extension gap. The distal femur and proximal tibia are typically resected to be parallel to a joint line 8, and thus perpendicular to mechanical axes 4, 5 as indicated at 10 and 12. Other cuts may be made depending on the components that are to be implanted. These include an anterior femoral cut 20, an anterior femoral chamfer cut 22, a posterior femoral chamfer cut 24, and a posterior femoral cut 26. A patella cut 28 may also be made to allow for replacement of the patellar articular surface. In a unicondylar knee replacement, only the medial or lateral side of the knee joint is resurfaced. Furthermore, the trochlear, or patellar bearing, surface of the femur is typically left intact in a unicondylar procedure. Unicondylar implant designs vary, but typically only distal femoral cut 10, posterior femoral chamfer cut 24, and posterior femoral cut 26 are needed to accommodate the unicondylar femoral implant.

In many cases it is desirable to observe movement of the joint before determining whether to reset the femur and proximal tibia in typical fashion. For example, a surgeon may determine, based on observed articulation of the joint, bone defects, patient age and patient condition, that an atypical resection angle is desirable. The surgeon may also observe soft tissues such as tendons and ligaments and determine that soft tissue balance requires atypical resections. Resection angle variations as small as one degree may impact the function of the joint. Systems and methods are needed which enable determination of resection planes intraoperatively to achieve soft tissue balance.

SUMMARY

A virtual implant placement method and a system are disclosed herein. The method and system enable determination of a first cut plane to resect a first bone. The first bone and a second bone are part of a joint. A second cut plane may also be determined to resect the second bone. The first and second bones may be resected in any order. The joint may be modelled intraoperatively to determine the cut planes. The method and system also enable intraoperative re-sizing of implants.

In an exemplary embodiment of the present disclosure, a virtual implant placement system for determining a first cut plane to resect a first bone is provided. The first bone and a second bone being part of a joint. The virtual implant placement system comprising a first tracking assembly supported by the first bone and operable to generate a first position data corresponding to a plurality of first positions of the first tracking assembly as the joint is articulated; a second tracking assembly supported by the second bone and operable to generate a second position data; a first implant model of a first implant, the first implant model linked to the first tracking assembly; a second model of one of a second implant and the second bone, the second model linked to the second tracking assembly; and a processing device determining the first cut plane based on the first model, the first position data, the second model, and the second position data.

In one example, the second position data corresponds to a plurality of second positions of the second tracking assembly as the joint is articulated.

In another example, the system further comprises a virtual joint and a goodness-of-fit function. The virtual joint defining a positional relationship between articulating surfaces of the first model and the second model. The processing device performs a plurality of permutations of the virtual joint. For each permutation the processing device articulates the virtual joint and computes a goodness-of-fit score and determines the first cut plane based on the permutation that yields an optimal score. In a variation thereof, the optimal score is the lowest score. In another variation thereof, the goodness-of-fit score comprises a maximum goodness-of-fit error, and the optimal score is the minimal maximum goodness-of-fit error. In yet another variation thereof, the goodness-of-fit function is weighed to favor permutations that reflect motion constraints of the joint. The motion constraints of the joint may be derived from the first position data and the second position data. The motion constraints may be provided to the processing device. The motion constraints may be selectable from a list presented with a viewing device. In yet another variation thereof, the virtual joint is constrained according to motion constraints of the joint. The motion constraints of the joint may be derived from the first position data and the second position data. The motion constraints may be provided to the processing system. The motion constraints may be selectable from a list presented with a viewing device.

In a further example, the virtual implant placement system further comprises a stabilized resection tool including an operator interface, a cutting tool, a plurality of linear actuators rotatably coupling the operator interface and the cutting tool, and a tracking assembly. The tracking assembly being operable to generate a third position data corresponding to the position of the cutting tool. The processing device actuates at least one of the plurality of linear actuators to align the cutting tool with the first cut plane.

In yet another example, the virtual implant placement system further comprises a guide surface adapted to guide a cutting tool. The processing device outputs adjustment parameters to align the cutting tool with the first cut plane. In a variation thereof, the virtual implant placement system further comprises a support base including a plurality of apertures configured to removably affix the support base to the first bone, and an adjustment mechanism supported by the support base and including a plurality of linear actuators. The linear actuators supporting the first tracking assembly and the guide surface. The linear actuators actuated according to the adjustment parameters to align the guide surface and the first cut plane. The adjustment parameters may be displayed with a viewing device to enable manual actuation of the linear actuators. The adjustment mechanism may further include a plurality of motors operable according to the adjustment parameters to actuate the plurality of linear actuators. In another variation thereof, the virtual implant placement system further comprises an adjustable cut block, a docking station, and a locking mechanism. The adjustable cut block including a cut block base. The guide surface adjustably coupled to the cut block base. The docking station including at least one driving mechanism for adjusting a position of the guide surface relative to the cut block base according to the adjustment parameters when the adjustable cut block is mounted onto the docking station. The locking mechanism locking the position of the cut block base relative to the guide surface. The adjustment parameters may be displayed with a viewing device to enable manual actuation of the driving mechanism. The driving mechanism may be automatically actuated according to the adjustment parameters.

In yet another example, the processing device also determines a second cut plane adapted to resect the second bone. The first cut plane and the second cut plane are determined independently so as to enable resectioning the first bone and the second bone in any order.

In yet still another example, the virtual implant placement system further comprises a viewing device. The processing device presents a virtual joint in the viewing device including a first visual indication of the first model and a second visual indication of the second model. The processing device alters the position of the first visual indication relative to the second visual indication in response to movement of the first tracking assembly relative to the first bone. The processing device determines the first cut plane when the virtual joint presented with the viewing device corresponds to the joint through an articulating motion of the joint. In one variation thereof, the processing device receives an input indicating that the virtual joint corresponds to the joint. In another variation thereof, the virtual implant placement system further comprises a sensing device to determine a joint landmark relative to the first bone and the second bone, wherein the virtual joint includes a landmark visual indication. The sensing device may comprise a trackable pointer. The sensing device may comprise a camera generating images of the joint. The landmark being identifiable in the images generated by the camera. In yet another variation, the virtual implant placement system further comprises a stabilized resection tool including an operator interface, a cutting tool, a plurality of linear actuators rotatably coupling the operator interface and the cutting tool, and a tracking assembly operable to generate a third position data corresponding to the position of the cutting tool. The processing device actuates at least one of the plurality of linear actuators to align the cutting tool with the first cut plane. In yet a further variation, the virtual implant placement system further comprises a guide surface adapted to guide a cutting tool. The processing device outputs adjustment parameters to align the cutting tool with the first cut plane. The virtual implant placement system may further comprise a support base including a plurality of apertures configured to removably affix the support base to the first bone, an adjustment mechanism supported by the support base and including a plurality of linear actuators, the linear actuators supporting the first tracking assembly and the guide surface, and the linear actuators actuated according to the adjustment parameters to align the guide surface and the first cut plane. The adjustment parameters may be displayed in the viewing device to enable manual actuation of the linear actuators. The adjustment mechanism may further include a plurality of motors operable according to the adjustment parameters to actuate the plurality of linear actuators. The virtual implant placement system may further comprise an adjustable cut block, a docking station, and a locking mechanism. The adjustable cut block including a cut block base adjustably coupled to the guide surface. The docking station including at least one driving mechanism for adjusting a position of the guide surface relative to the cut block base according to the adjustment parameters when the adjustable cut block is mounted onto the docking station. The locking mechanism locking the position of the cut block base relative to the guide surface. The driving mechanism may be automatically actuated according to the adjustment parameters. In still another variation thereof, the processing device also determines a second cut plane adapted to resect the second bone. The first cut plane and the second cut plane being determined independently so as to enable resectioning the first bone and the second bone in any order. In still yet another variation thereof, the virtual implant placement system further comprises a first support device including a first base having a first plurality of apertures configured to removably affix the first base to the first bone, and a first plurality of linear actuators rotatably coupling the first base and the first tracking assembly to move the first tracking assembly relative to the first bone. In still a further variation thereof, the viewing device is positioned relative to the joint such that the joint and the virtual joint presented in the viewing device can be viewed simultaneously from a first direction. In still a further variation thereof, the viewing device displays simultaneously the virtual joint and a visual representation of the joint.

In another exemplary embodiment of the present disclosure, a virtual implant placement system for determining a first cut plane to resect a first bone is provided. The first bone and a second bone being part of a joint. The system comprising first position indicating means for generating a first position data corresponding to a plurality of first positions of the first bone as the joint is articulated; second position indicating means for generating a second position data corresponding to a second position of the second bone; guiding means adapted to align a cutting tool with the first cut plane; and determining means for determining the first cut plane.

In one example, the determining means comprise a virtual joint and a goodness-of-fit function. The virtual joint defining a positional relationship between articulating surfaces of the first model and the second model. The determining means performs a plurality of permutations of the virtual joint. For each permutation the processing device articulates the virtual joint and computes a goodness-of-fit score. The processing device determines the first cut plane based on the permutation that yields an optimal score. In a variation thereof, the optimal score is the lowest score. In another variation thereof, the goodness-of-fit score comprises a maximum goodness-of-fit error, and the optimal score is the minimal maximum goodness-of-fit error. In still another variation thereof, the goodness-of-fit function is weighed to favor permutations that reflect motion constraints of the joint. The motion constraints of the joint may be derived from the first position data and the second position data. The motion constraints may be provided to the determining means. The motion constraints may be selectable from a list presented with a viewing device. In yet still another variation, the virtual joint is constrained according to motion constraints of the joint. The motion constraints of the joint may be derived from the first position data and the second position data. The motion constraints may be provided to the determining means. The motion constraints may be selectable from a list presented with a viewing device.

In another example, the virtual implant placement system further comprises presentation means for presenting a virtual joint. The virtual joint including a first visual indication of a first implant and a second visual indication corresponding to a second implant or the second bone. The determining means alters the position of the first visual indication relative to the second visual indication in response to movement of the first position indicating means relative to the first bone and determines the first cut plane when the virtual joint presented in the viewing device corresponds to the joint. In a variation thereof, the presentation means presents, simultaneously, the virtual joint and a visual representation of the joint. In another variation, the presentation means is positioned relative to the joint such that the joint and the virtual joint can be viewed simultaneously from a first direction. In a further variation, the determining means further include a sensor providing a joint landmark indication.

In a further example, the guiding means are rotatably coupled to the cutting tool. In still another example, the guiding means include a base component and a guide surface. The position of the guide surface relative to the base component is remotely adjustable before the guiding means are mounted onto the first bone. In yet a further example, the guiding means include a base component, a guide surface, and a plurality of adjustment components rotatably coupling the guide surface to the base component.

In a further exemplary embodiment of the present disclosure, a virtual implant placement method for determining a first cut plane to resect a first bone is provided. The first bone and a second bone being part of a joint. The method comprising the steps of tracking a first position of the first bone with a first tracking device adjustably coupled to the first bone; tracking a second position of the second bone with a second tracking device coupled to the second bone; providing a virtual joint including a first visual indication of a first implant and a second visual indication of one of a second implant and the second bone; presenting the virtual joint with a viewing device; altering the position of the first visual indication relative to the second visual indication in response to movement of the first tracking device relative to the first bone; and determining the first cut plane when the virtual joint presented in the viewing device corresponds to the joint through an articulating motion of the joint.

In one example, the virtual implant placement method further comprises the step of receiving an input indicating that the virtual joint corresponds to the joint. In another example, the virtual implant placement method further comprises the step of sensing with a sensing device a joint landmark relative to the first bone and the second bone. The virtual joint includes a landmark visual indication. In a variation thereof, the sensing device comprises a trackable pointer. In another variation thereof, the sensing device comprises a camera generating images of the joint, and the joint landmark is identifiable in the images generated by the camera.

In a further example thereof, the virtual implant placement method further comprises the step of navigating a stabilized resection tool having a cutting tool to align the cutting tool with the first cut plane. In a variation thereof, the virtual implant placement method further comprises the step of positionally adjusting a guide surface adapted to guide a cutting tool to align the cutting tool with the first cut plane.

In yet a further example thereof, the virtual implant placement method further comprises the step of positioning the viewing device such that the virtual joint and the joint are simultaneously viewable from a first direction. In still a further example thereof, the virtual implant placement method further comprises the step of simultaneously presenting with the viewing device the virtual joint and a visual representation of the joint. In yet still a further example thereof, the virtual implant placement method further comprises the step of determining a second cut plane to resect the second bone. The first cut plane and the second cut plane being determined independently of each other so as to enable resectioning the first bone and the second bone in any order.

In yet a further exemplary embodiment of the present disclosure, a virtual implant placement method for determining a first cut plane to resect a first bone is provided. The first bone and a second bone being part of a joint. The method comprising the steps of tracking a first position of the first bone with a first tracking device adjustably coupled to the first bone;

tracking a second position of the second bone with a second tracking device coupled to the second bone; providing a virtual joint and a goodness-of-fit function to generate a goodness-of-fit score; performing a plurality of permutations of the virtual joint; for each permutation, articulating the virtual joint and computing the goodness-of-fit score, and determining the first cut plane based on the permutation that yields an optimal score.

In one example, the virtual joint includes a first implant model and a second model of one of a second implant and the second bone. The virtual joint defining a virtual positional relationship between articulating surfaces of the first model and the second model corresponding to an actual positional relationship between the first tracking device and the second tracking device. Each permutation changing the virtual positional relationship. In another example, the optimal score is the lowest score. In a further example, the goodness-of-fit score comprises a maximum goodness-of-fit error and the optimal score is the minimal maximum goodness-of-fit error. In still another example, the virtual implant placement method further comprises the steps of articulating the joint, deriving motion constraints of the joint from the automatically tracked first position and the automatically tracked second position, and at least one of weighing the goodness-of-fit function to favor permutations that reflect the motion constraints and constraining the virtual joint according to the motion constraints. In yet still a further example, the virtual implant placement method further comprises the steps of providing motion constraints of the joint and at least one of weighing the goodness-of-fit function to favor permutations that reflect the motion constraints and constraining the virtual joint according to the motion constraints. In yet still another example, the virtual implant placement method further comprises the step of generating adjustment parameters to align a guide surface configured to align a cutting tool with the cut plane. In still yet another example, the virtual implant placement method further comprises the step of determining a second cut plane to resect the second bone. the first cut plane and the second cut plane being determined independently of each other so as to enable resectioning the first bone and the second bone in any order.

In still yet a further exemplary embodiment of the present disclosure, a digital storage device operable with a processing system to determine a first cut plane to resect a first bone is provided. The first bone and a second bone being part of a joint. The storage device comprising a first model of a first implant, a second model of one of a second implant and the second bone, the first model and the second model having articulating surfaces; a data structure defining a virtual joint comprising the first model, the second model, and a positional relationship between the articulating surfaces of the first model and the second model; a goodness-of-fit function; a first processing sequence permutating the positional relationship; a second processing sequence articulating the virtual joint and calculating a goodness-of fit score after each permutation; a third processing sequence defining the cut plane according to the permutation which yields an optimal goodness-of-fit score; and a fourth processing sequence outputting adjustment parameters configured to align a guide surface with the cut plane.

The features of the invention, and the manner of attaining them, will become more apparent and the invention itself will be better understood by reference to the following description of the disclosed embodiments taken in conjunction with the accompanying drawings. These above mentioned and other features of the invention may be used in any combination or permutation.

BRIEF DESCRIPTION OF THE DRAWINGS

FIG. 1 is an anterior elevation view of a tibia and a femur showing axes of the knee joint;

FIG. 2 is a plan view of a knee joint showing typical bone cuts for replacing the joint surfaces;

Figure 3:
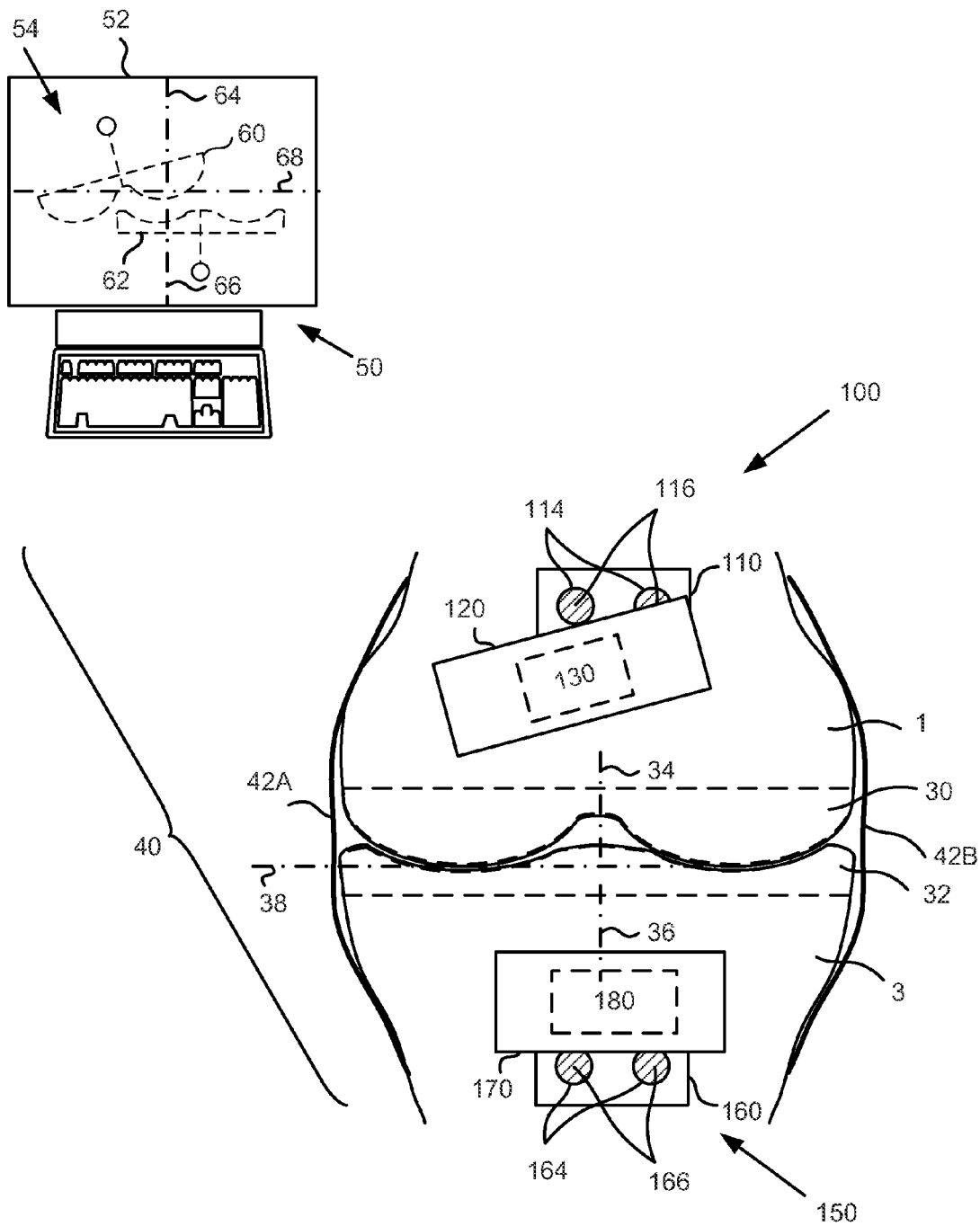
FIG. 3 is a schematic view of an embodiment of a positioning system showing an anterior elevation view of a knee joint, a computer display showing images of two implant models, and support devices including trackable support bodies.

Corresponding reference characters indicate corresponding parts throughout the several views. Although the drawings represent embodiments of the present disclosure, the drawings are not necessarily to scale and certain features may be exaggerated to better illustrate and explain the embodiments. The exemplifications set out herein illustrate embodiments of the invention in several forms and such exemplification is not to be construed as limiting the scope of the invention in any manner.

DETAILED DESCRIPTION

The embodiments discussed below are not intended to be exhaustive or limit the invention to the precise forms disclosed in the following detailed description. Rather, the embodiments are chosen and described so that others skilled in the art may utilize their teachings.

A virtual implant placement method and system are disclosed herein. One embodiment of the system enables a surgeon to determine a desired position of an implant relative to a bone of a joint based on joint kinematics. Another embodiment of the system enables a surgeon to determine the desired positions of two implants based on joint kinematics and to resection the bones in any order. Both embodiments comprise two trackable tracking assemblies coupled to the bones to intraoperatively characterize the joint. The desired position(s) of the implant(s) is(are) then determined based on the characteristics of the joint. Cut planes are determinable according to the implant geometries and the desired positions. Furthermore, the system may be used to simulate the joint with digital models of the implants and to intraoperatively select different implant sizes. Various devices are disclosed herein operable with the tracking assemblies to align cut guides with the desired cut planes. In a further embodiment, a stabilized resection tool may be used to resection a bone. In a yet further embodiment, a viewing device may be positioned near the joint to enable a surgeon to simultaneously view the joint and a model of the joint.

Tracking assemblies may comprise any known tracking technology. Non-limiting examples of tracking technologies include acoustic, electromagnetic, inertial, and optical. Tracking assemblies may include appropriate fiducials, coils, inertial sensors and other tracking components of such tracking technologies. Tracking assemblies may also include electronic components to convert signals received from the tracking components and to transmit representative signals to a signals processor. A signals processor may include optical sensors, a wireless receiver, and/or other tracking components which cooperate with tracking and electronic components in the tracking assemblies to obtain indications of their position (e.g. location and/or orientation). For example, electromagnetic tracking technology comprises a signal generator and coils in the tracking assembly which generate position signals representative of their position relative to the signal generator. The position signals may be digitized and transmitted wirelessly to a receiver in the signals processor. Acoustic tracking technology operates in a similar manner. An acoustic tracking assembly may include materials of specific density or characteristics for reflecting acoustic waves, and the acoustic waves reflected from the materials provide position information to an acoustic sensor. In optical tracking technology, tracking assemblies include fiducials detectable by a remote optical sensor or camera. The optical sensor generates position signals of the fiducials. The position of the tracking assembly is then determined by triangulation. Inertial tracking technology comprises inertial sensors such as accelerometers and gyroscopes which detect motion based on motion of an embedded proof mass and output acceleration, rate and/or inclination signals. The signals can be integrated to track position changes based on dead-reckoning techniques. Static inclination signals do not require integration. Other sensors may also be used alone or in combination with the above to provide redundant measurements, to compensate for sensing technology deficiencies such as drift, and to provide a secondary position indication when the primary technology is not adequate (e.g., when line-of-sight is lost in an optical system or magnetic interference is present in an electromagnetic system). Position signals may be filtered, sampled, digitized, and transmitted by a wireless transmitter. The signals may also be transmitted by hard-wired connections for processing by a processing system. Exemplary tracking technologies are disclosed in U.S. Pat. No. 6,499,488 and U.S. Pat. Publ. Nos. 2003/0078003 and 2008/0065085, 2009/0143670, and 2009/0138019, which are incorporated by reference herein in their entirety.

A tracking assembly may be attached to, or incorporated in, a support body mountable on a bone of the joint to provide a reference position of the bone. The support body may also be adjustably coupled to a support base which is mountable on the bone. An adjustment mechanism may be used to attach the support body to the support base thereby enabling adjustment of the position of the tracking assembly relative to the support base and the bone. The adjustment mechanism may permit translation and/or orientation adjustments which may be detected and tracked. Furthermore, the support body may support a cut block comprising a guide surface configured to guide the position of a cutting tool.

In an exemplary embodiment, the virtual implant placement system utilizes two tracking assemblies to characterize the joint kinematically after the tracking assemblies are mounted on the bones. The tracking assemblies and a signals processor generate position signals corresponding to the positions of the tracking assemblies based on an arbitrary origin of a coordinate system. The origin may be a designated point in one of the tracking assemblies to simplify computations. The signals processor may also convert position signals to position data so that the data may be wirelessly transmitted. If the tracking assemblies are capable of generating position signals without a signals processor, the signals processor may be omitted and the position signals may be transmitted to a processing system directly by the tracking assemblies. Integrated circuits comprising inertial and other sensors, e.g. micro-electro-mechanical systems (MEMS), may be combined in small packages with memory, a microprocessor, a battery and a wireless transmitter. The microprocessor can then be programmed to wirelessly transmit position data such as inclination relative to gravity, orientation relative to the earth or a magnetic field, and orientation and location based on dead-reckoning methods. Of course, the microprocessor may also be programmed to transmit digitized position signals which are then further processed to determine the position of the tracking assembly.

In the exemplary embodiment, a processing system receives position signals or position data and computes a joint model based on position measurements taken while the joint is articulated. Kinematic constraints may be imposed on the joint by the surgeon. For example, the surgeon may input joint constraints such as mechanical axis orientation adjustments, maximum flexion or extension angles and so forth. The processing system includes storage media, navigation and simulation software embedded in the storage media, and digital models of objects which may include bones, implants, support devices, support bodies, medical tools and instruments, and any other devices whose geometric measurements are needed to fit implant models and determine resection planes. Simulation software computes joint characteristics based on the geometries of the implants and joint kinematics to determine the desired positions of the implants and cut planes. Navigation software may be used to determine the adjustments necessary to align guide surfaces and the cut planes so that the implants may be implanted in the desired positions. Adjustments may be manual or automatic and may be made to adjustment mechanisms of support devices, remotely adjustable cut blocks, stabilized resection tools, and any other devices configured to control the position of a cutting instrument. References to position adjustments are intended to include location adjustments, orientation adjustments, or both location and orientation adjustments and do not necessarily require changes in both location and orientation. Rather, such reference simply denotes adjustment by translation in one or more of three directions and rotation in one or more of three directions.

The modelling software may present images of the implants and bones with a viewing device. The images and implant dimensions may be referred to as digital models or simply models. Selection of support devices, a tracking assembly, cut blocks and other devices to be used in a selected surgical procedure determines the spatial relationship between a tracking assembly and a cut plane. A model may be automatically linked to a tracking assembly once selected based on the known geometric parameters defining the spatial relationship between them. As the tracking assembly moves during joint articulation, the model moves in a corresponding manner. Different views of the model are presented as the bone rotates. A catalogue of devices, implants, and bones with corresponding models may facilitate selection. A user may change implant selections intraoperatively, and the modelling software may then present new models in the viewing device. The modelling software does not require images of bones obtained pre-operatively such as X-rays and CAT scans although such images may be used to pre-select objects and optimize the intraoperative procedure.

Figure 4:
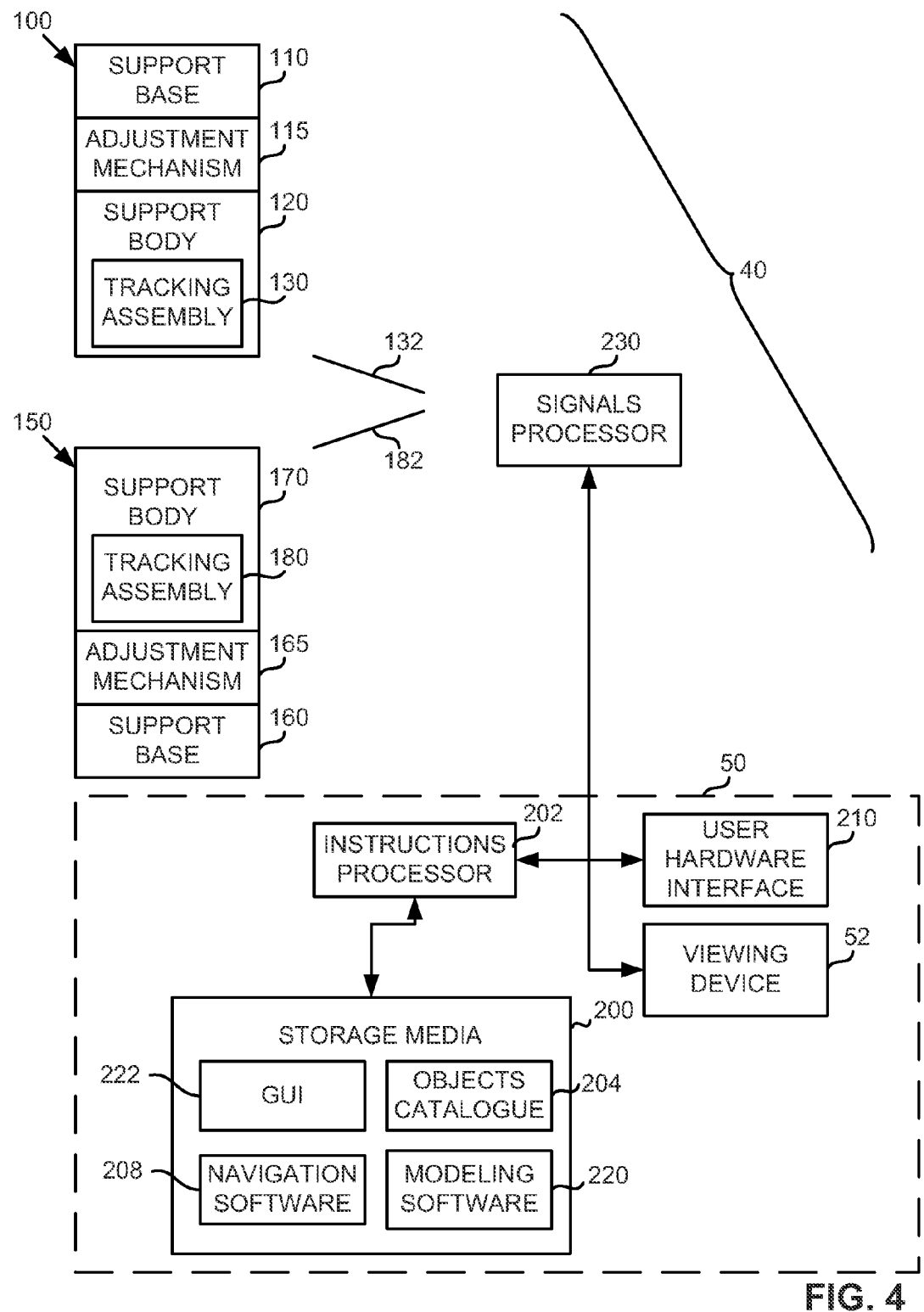
FIG. 4 is a block diagram of the positioning system of FIG. 3.
Figure 10:
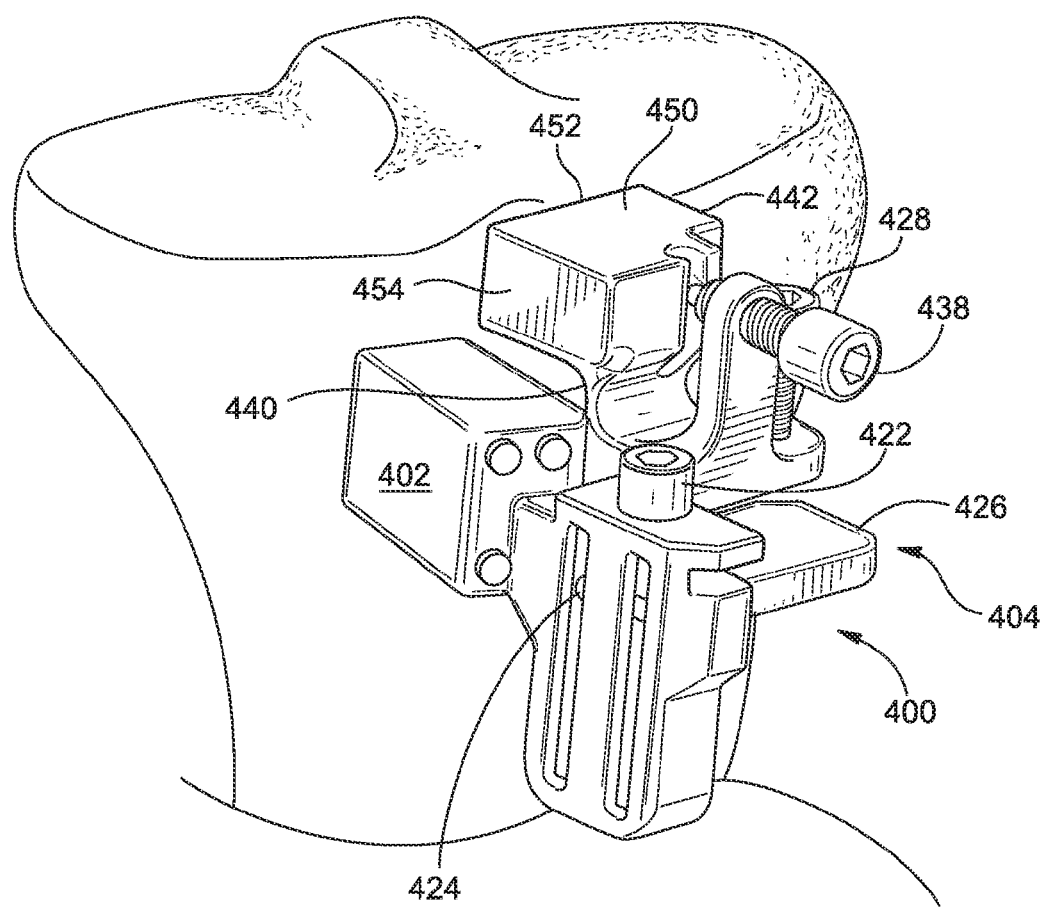
FIG. 10 is a perspective view of a support device.
Figure 17:
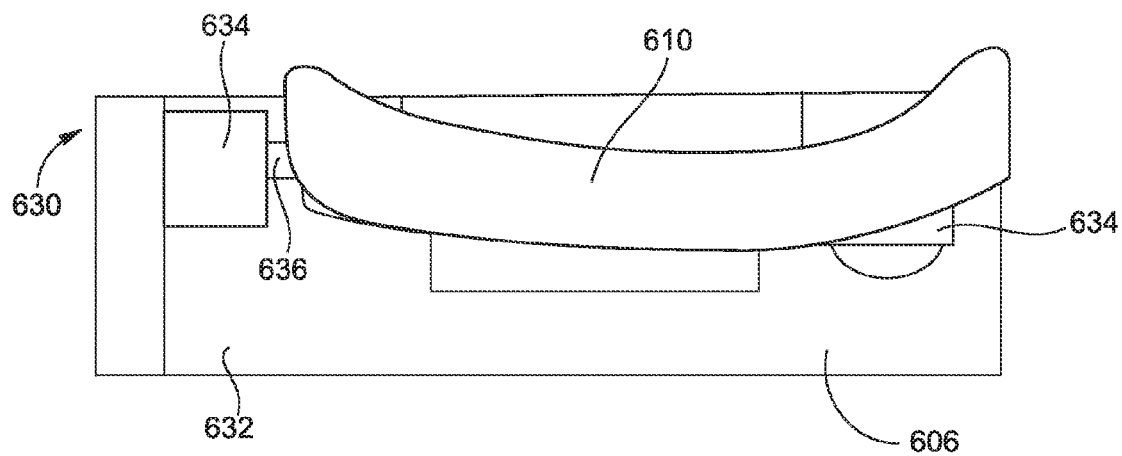
FIGS. 17 and 18 are plan and elevation views of a remotely adjustable cut block operable with the positioning system of FIG. 16.
Figure 18:
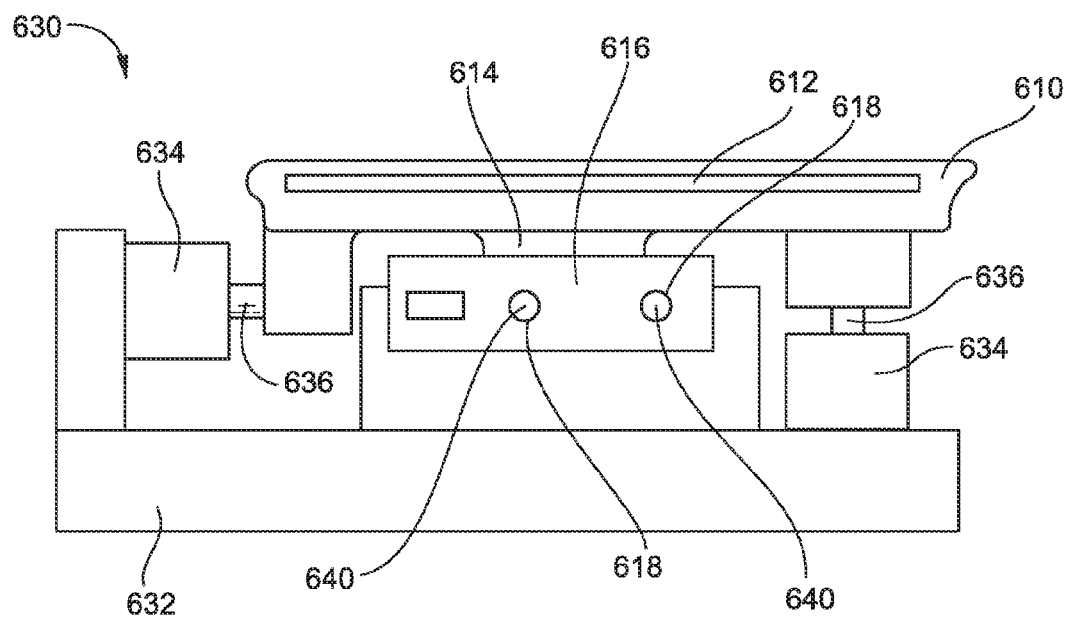
Figure 20:
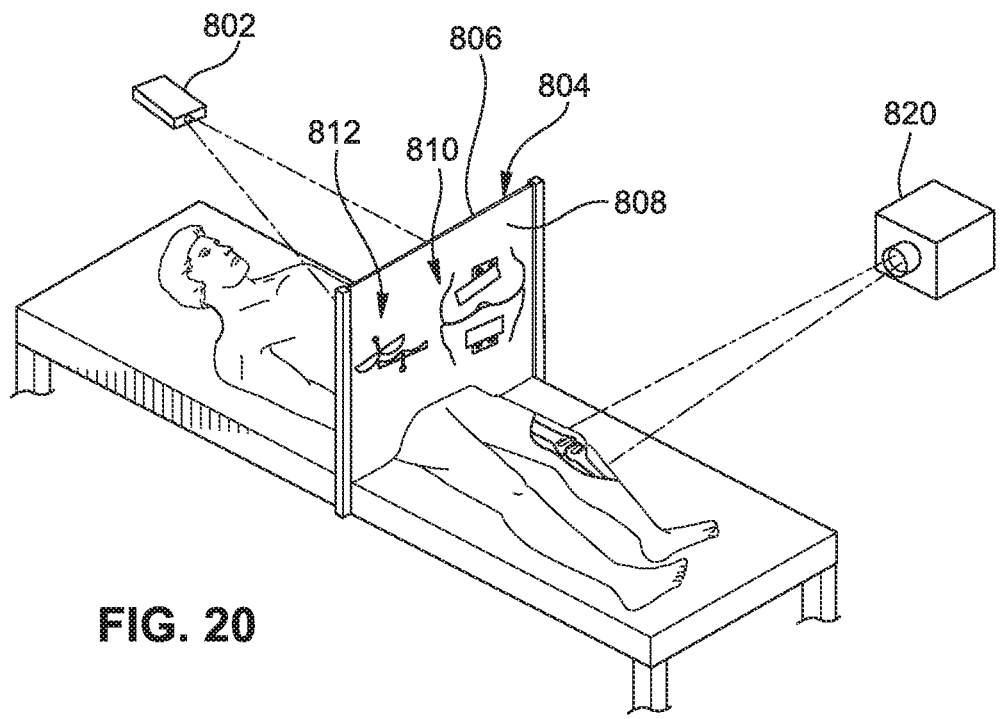
FIGS. 20 and 21 are perspective views of a patient on an operating table, and a projector projecting images on a viewing screen.
Figure 21:
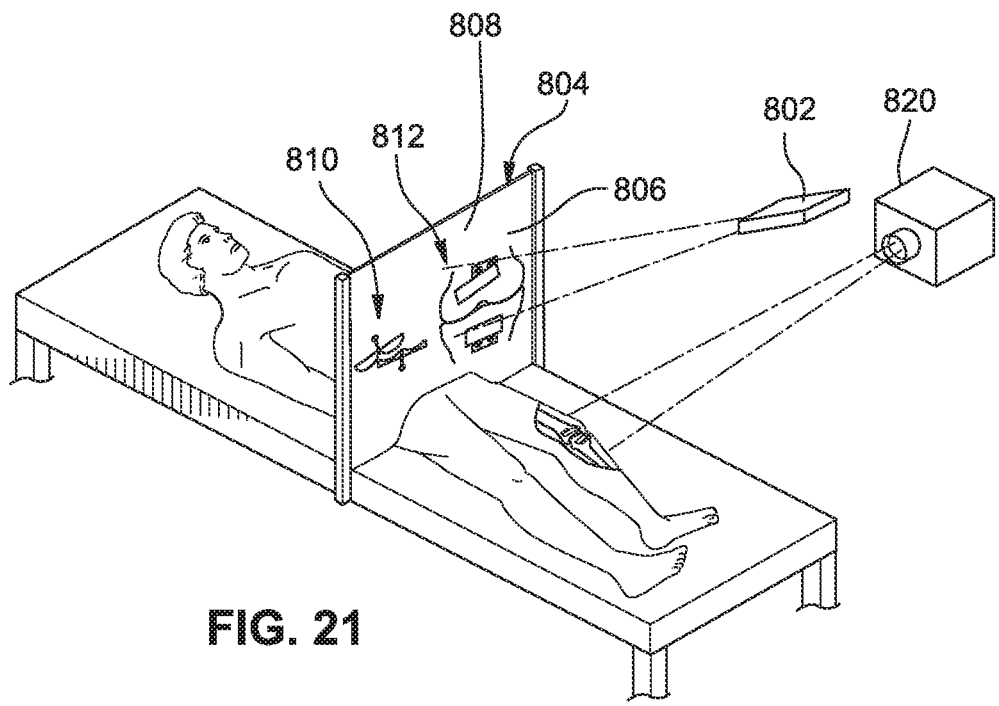

The above description of exemplary embodiments will now be described with reference to the figures. Referring to FIGS. 3 and 4, an embodiment of a virtual placement system will be described. FIG. 3 depicts components of the system, denoted by numeral 40, with reference to bones 1 and 3 and soft tissue 42A and 42B, illustratively ligaments. System 40 includes a processing system 50, illustratively a computer, and a viewing device 52, illustratively a computer screen. Other exemplary viewing devices include projectors with a viewing screen 804 such as is shown in FIGS. 20 and 21, hand-held display devices, tablet devices, and other suitable devices for displaying images. A viewing device may be positioned near the joint so as enable simultaneous viewing of the joint and the models displayed on the viewing device. Images may also be presented in eyeglasses, e.g. lenses mounted in eyewear or attached to headgear, or faceshields, so that the surgeon can continue to view the images without orienting his/her head in any particular direction. Also shown are first and second support devices 100, 150 including first and second support bases 110, 160, support bodies 120, 170 and first and second tracking assemblies 130, 180. An image 54 is shown with viewing device 52. Support devices 100 and 150 are mounted on bones 1 and 3. Support bases 110 and 160 comprise apertures 114 and 164 provided to receive support members 116 and 166 to detachably mount support bases 110 and 160 to bones 1 and 3. Adjustment mechanisms 115 and 165 (shown in FIG. 4) adjustably couple support bases 110 and 160 to support bodies 120 and 170. Exemplary adjustment mechanisms are also shown in FIGS. 10, 17 and 18.

FIG. 3 also shows, in phantom, a pair of implants 30 and 32 superimposed on bones 1 and 3 to illustrate a desired position of implants 30 and 32 after surgery. Axial lines 34, 36 and 38 represent the desired alignment axes of implants 30 and 32. Image 54 in viewing device 52 illustrates a pair of images 60 and 62 of implant models, and lines 64, 66 and 68 reflecting the virtual positions of axial lines 34, 36 and 38. As explained with reference to FIGS. 7A-8D, the positions of images 60 and 62 correspond to the positions of support bodies 120 and 170. As the support bodies move, the implant images move in a corresponding manner. The support bodies can thus be moved to align images 60 and 62 until they correspond with the desired positions of implants 30 and 32. As shown in FIG. 3, line 34 is parallel to mechanical axis 4, line 36 is parallel to mechanical axis 5, and line 38 is parallel to joint line 8. However, lines 34 and 36 and 38 may be selected to adjust the mechanical alignment of bones 1 and 3. In some patients, the mechanical axes are not perfectly aligned with each other and the surgeon may determine a priory to change the mechanical axes of bones 1 and 3 to correct the patient's leg alignment. Implant models comprise images as well as dimensions which the processing system utilizes to link models to each other thereby determining overall dimensions between tracking assemblies, support devices, cut blocks, other medical implements, and guide surfaces. An implant model comprises at least one engagement surface configured to engage an engagement surface of a bone. The engagement surface of the bone is a surface created by resectioning the bone along a cut plane. The cut plane is aligned with the engagement surface of the implant (when the implant is properly positioned on the resected bone) and with a guide surface provided by a cut guide (once the cut guide is properly positioned on the bone to facilitate resectioning of the bone).

Images 60 and 62 may have any shape suitable for indicating the configuration of the tracking assemblies relative to one or more joint parameters (e.g. gaps, landmarks, and the like). As shown, images 60 and 62 include three graphical objects each: a shape analogous to the shape of an implant, a circle, and a line connecting the shape of the implant with the circle. The circle represents a known point in a tracking assembly, and the line represents the orientation of a cut plane. The distance from the circle to the implant along the line represents the distance between the tracking assembly and the cut plane which is based on the known geometric relationship of the tracking assembly and the implant. Thus, images 60 and 62 represent the relative positions of implants 30 and 32 to tracking assemblies 130 and 180, and image 54 represents their positions with reference to the desired axial lines of the joint. In one embodiment, the spatial relationship between the positions of the implant images and the axial lines is determined according to joint kinematics as described further below. Alternatively, the relationship may also be determined by contacting bone landmarks with a tracked pointer as is well known in the art. The spatial relationships between the tracked pointer and the tracking assemblies, determined when the pointer contacts a landmark, establish the spatial relationship between the tracking assemblies and the landmark, which relationship is then transposed to the viewing device as the relationship between the model images and the virtual axial lines. As described elsewhere in this disclosure, camera images may also be processed to identify the bones and joint landmarks from which the position of joint parameters may be determined to construct a joint model.

FIG. 4 depicts a block diagram of system 40 comprising processing system 50, support devices 100, 150, and a signals processor 230 which senses or receives signals 132 and 182 to track the positions (e.g. location and/or orientation) of tracking assemblies 130 and 180. System 50 further includes an instructions processor 202, a storage device 200 and a user hardware interface 210. System 50 may be a stand-alone computer or a networked system with distributed components. Storage media 200 may comprise, for example, hard disks, flash memory, random access memory, compact disks, digital video disks, storage media distributed in a network environment, and storage media accessible remotely via the internet. Processor 202 executes processing sequences embedded in storage media 200 such those described with reference to FIG. 22. Processing sequences may be combined and described into software components, based on their overall function for ease of explanation, such as navigation software 208, modelling software 220, and instructions configured to provide a graphical user interface, illustratively GUI 222. GUI 222 functions in cooperation with user hardware interface 210 to enable user selection of features of the navigation and modelling software. Navigation software 208 may comprise instructions for automatically adjusting adjustment mechanisms, instructions to receive user inputs concerning desired adjustments, instructions to output adjustment parameters, and instructions to control the position of a stabilized resection tool, as well as other processing sequence configured to facilitate movement of a medical implement or component from one position to another. Modelling software 220 may comprise model construction instructions, instructions for displaying models with viewing device 52, instructions for transmitting position data or signals from signals processor 230, instructions for receiving inputs from user hardware interface 210 or operating GUI 222 with viewing device 52 to receive additional user instructions, and other instructions for spatially relating medical implements or components to each other and to bones.

Catalogue 204 and data structures for establishing spatial relationships between objects are also embedded in storage media 200. Objects in catalogue 204 may comprise models of implants, bones, support devices, medical instruments such as cut blocks, and the like. The catalogue may simply comprise a plurality of software objects stored in the storage media which may be individually selected by a user. Objects may be selected by pointing to a catalogue image with a pointing device or entering a model number with a keyboard, or in any other suitable manner. An exemplary device for generating models of bones and other objects is disclosed in U.S. Pat. Publ. Nos. 2007/0156066 which is incorporated by reference herein in its entirety. Data structures associated with modelling and navigation software link models to define spatial parameters and relationships between bones and medical implements based on their models. The logical relationship between the models supports their manipulation such as when different views of the models are presented as the joint is articulated or when implant models are repositioned as tracking assemblies are repositioned relative to the bones. Models include dimensions from which wire-mesh three-dimensional models may be constructed and may also comprise images. According to the embodiments described herein, the joint is characterized to construct a joint model which establishes the spatial relationship between the bones forming the joint. The joint model parameters vary depending on the joint being characterized. A knee joint may include parameters such as the mechanical axes of the tibia and femur, the joint line, gap distances between the condyles and tibial plateau, and perhaps soft tissue tensions and other parameters. A hip joint may include parameters such as the center of rotation of the femur, the pelvic plane, and the leg length. Joint models may also include range of motion constraints.

In one embodiment of the virtual placement method, the surgeon mounts support devices 100 and 150 in somewhat arbitrary positions on bones 1 and 3. The positions are somewhat arbitrary because while the actual mounting positions do not need to be predetermined, the mounting positions should be within the range of adjustment of adjustment mechanisms. The positions of support bodies 120 and 170 are not initially known but, due to known geometric dimensions, the position of one relative to the other is determinable by processing system 50. In this embodiment, the surgeon articulates the joint through various motions to enable processing system 50 to collect motion data to define motion constraints. Motion information may be combined with additional constraints input from the surgeon. Processing system 50 then uses the motion data and motion constraints to characterize the joint relative to the tracking assemblies and determine desired implant positions. In an alternative embodiment, a tracked pointer may be used to supplement visual and computational techniques described herein to characterize the joint. The tracked pointer may be used to contact a joint landmark and define a spatial relationship between the landmark and the tracking assemblies which serves to relate the tracking assemblies to the joint characteristics. In another alternative embodiment, imaging technologies can be used to identify landmarks in both bones which are then contacted by the tracked pointer to establish the spatial relationship. In yet another embodiment, a camera may be used to digitize the joint in motion and support devices mounted on the bones to define the spatial relationship between them. An exemplary camera is shown in FIGS. 20 and 21 and denoted by numeral 820.

Once the joint has been characterized, processing system 50 can display images 60 and 62 relative to axial lines 64, 66 and 68 and the surgeon can observe the movement of images 60 and 62 as he/she articulates the joint. If the support devices are adapted to support guide surfaces, adjustments necessary to align the guide surfaces with the desired cut planes have to be determined, and then the adjustment mechanisms can be properly adjusted. The adjustments may be made iteratively by the surgeon as he/she observes the movement of the models and contrasts the relationship of the models on the viewing device to the relationship of the bones in the joint. The surgeon may adjust adjustment mechanisms 115 and 165 (which move support bodies 120 and 170, tracking assemblies 130 and 180, and cause movement of images 60 and 62) until image 54 corresponds to the surgeon's view of the real joint. Once the adjustments have been made, the surgeon can once again articulate the real joint to verify that the virtual joint articulates in the desired manner. The surgeon may manually make the adjustments or may input adjustment instructions which the navigation software interprets to automatically adjust the adjustment mechanisms. A viewing device suitable to facilitate simultaneous observation of the models and the real joint is described with reference to FIGS. 20 and 21. In an alternative embodiment, the navigation software calculates the necessary adjustments and causes the instructions processor to output adjustment information or automatically adjust the adjustment mechanisms. In a further embodiment, the navigation software controls a stabilized resection tool to align its cutting tool with the desired resection plane. A stabilized resection tool is described with reference to FIGS. 14 and 15.

Figure 5:
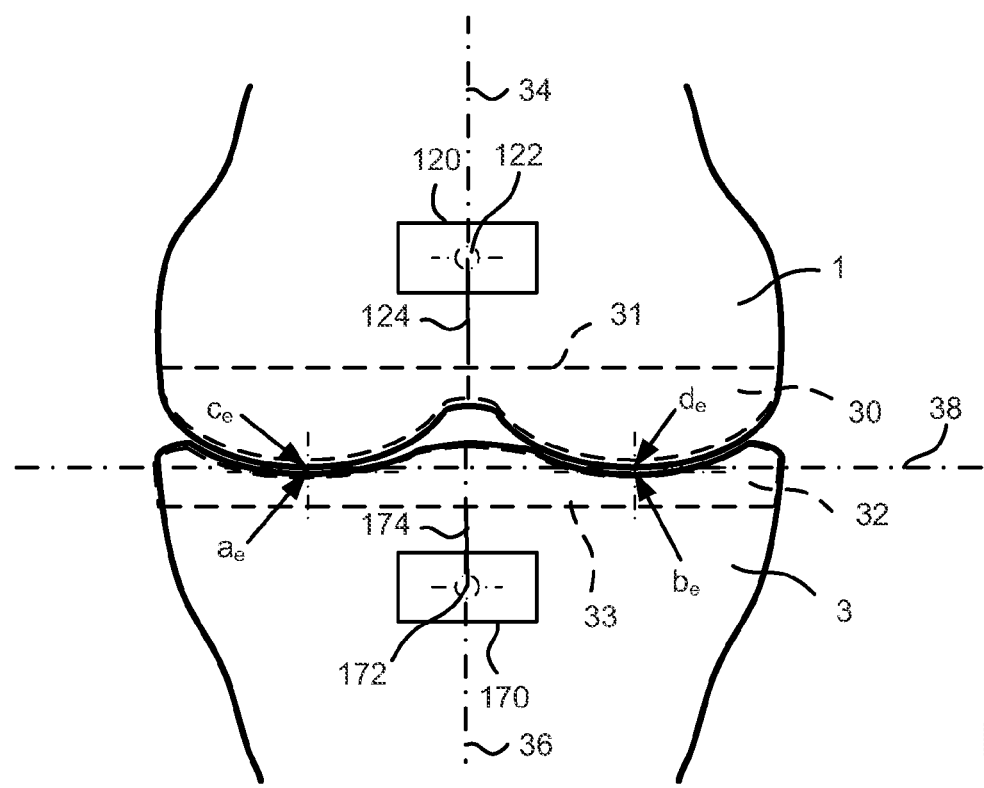
FIGS. 5 and 6 are anterior elevation and plan views of a knee joint showing implants, in phantom, and knee joint characteristics.
Figure 6:
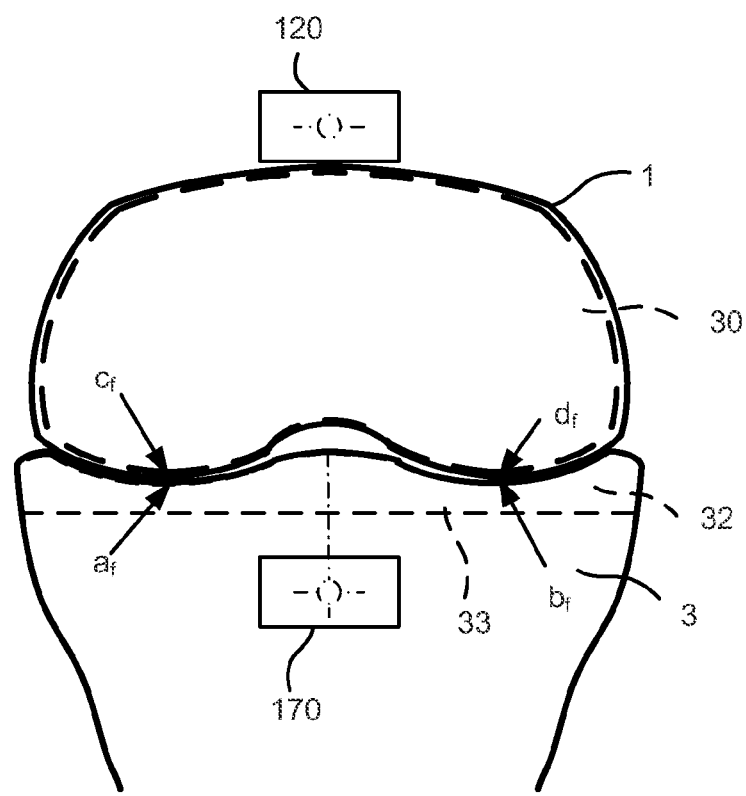

Referring to FIGS. 5 and 6, modelling characteristics are shown in relation to bones 1 and 3. As described above, axial lines 34, 36 and 38 indicate the desired mechanical axis of the bones and the joint line. Surfaces 31 and 33 represent the surfaces of implants 30 and 32 which will be adjacent to the resected bone after implantation. Thus, surfaces 31 and 33 are parallel to the desired cut planes of bones 1 and 3. The length of a line 124 shows the distance from a predetermined point 122 in body 120 to surface 31. The length is determinable upon selection of implant 30, support device 100, and any other components necessary to position a cut guide. Embodiments of support devices including cut guides and supporting cut blocks are shown with reference to FIGS. 16 and 19. The length of a line 174 shows the distance from a predetermined point 172 in body 170 to surface 33. The length is determinable upon selection of implant 32, support device 150, and any other components necessary to position a cut guide. Exemplary landmarks in the lateral and medial condyles and the tibial plateau of a knee joint in extension are denoted by the symbols $a_e$, $b_e$, $c_e$ and $d_e$. Exemplary landmarks in the lateral and medial condyles and the tibial plateau of the knee joint in flexion are denoted by the symbols $a_f$, $b_f$, $c_f$ and $d_f$. These or any other landmarks enable a surgeon to characterize the joint. For example, the distance between points $a_e$ and $c_e$ characterize a joint gap and points $b_e$, and $d_e$ characterize another joint gap. The surgeon can observe these gaps and then observe a joint model in a reviewing device to confirm that the joint model adequately represents the gaps. Upon confirmation, the surgeon may resect the bones according to the cut plane positions indicated by the joint model.

Figure 7A:
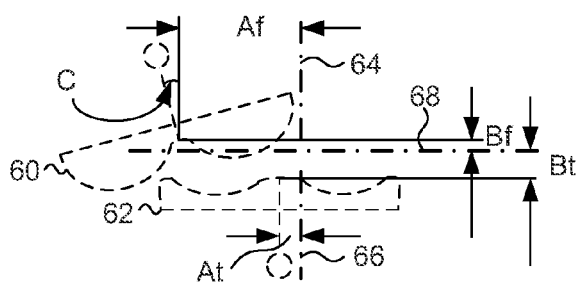
FIGS. 7A to 7D are conceptual representations of images of two implant models showing their relative positions in a coordinate system.
Figure 8A:
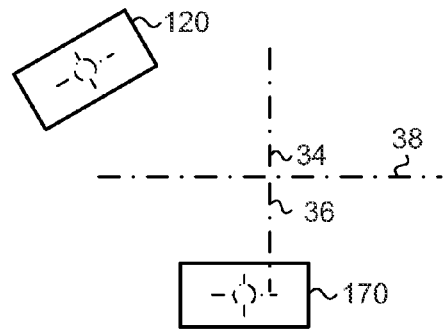
FIGS. 8A to 8D are block diagrams of tracked support bodies showing their relative positions in a coordinate system in relation to the images shown in FIGS. 7A to 7D.

Referring now to FIGS. 7A to 8D, representations of models and the positions of support bodies 120 and 170 are shown side-by-side to illustrate adjustments of support bodies 120 and 170 which modify the images shown with a viewing device. FIGS. 7A and 8A illustrate images 60 and 62 relative to axial lines 64, 66 and 68, support bodies 120 and 170 relative to desired axial lines 34, 36 and 38 and adjustment parameters. Adjustment parameters between the desired positions of the implants and axial lines 64, 66 and 68 (defined by the processing system upon articulation of the joint) are denoted by the symbols C (indicating angular adjustment of support body 120), Af (indicating medial/lateral adjustment of support body 120), At (indicating medial/lateral adjustment of support body 170), Bf (indicating proximal/distal adjustment of support body 120), and Bt (indicating proximal/distal adjustment of support body 170). In an alternative embodiment, support bodies 120 and 170 may be shown relative to the actual joint line and mechanical axes of the bones, and any desired modifications of the joint may be taken into account by changing adjustment parameters. Four translation and one rotation parameters are illustrated for simplicity. Since a support device may change the location and/or orientation of the support body relative to the support base in up to six degrees of freedom, up to six adjustment parameters may be provided for each support device.

Figure 7B:
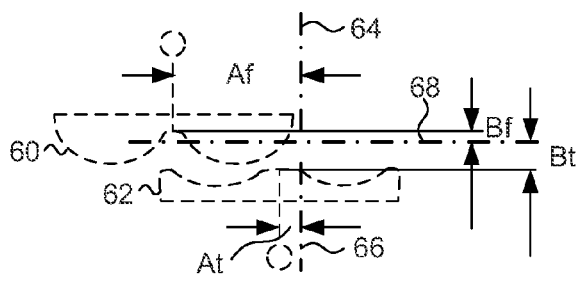
Figure 8B:
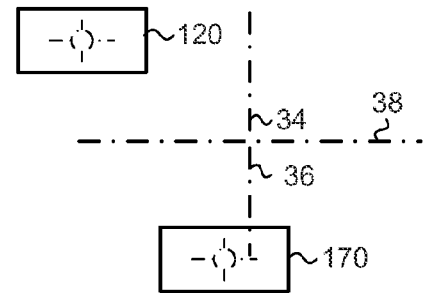
Figure 7C:
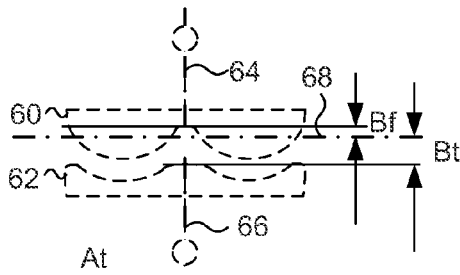
Figure 8C:
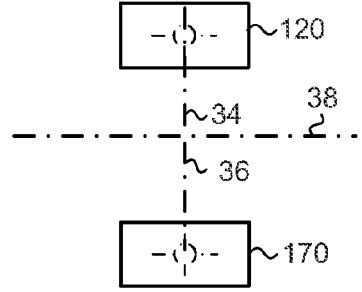
Figure 7D:
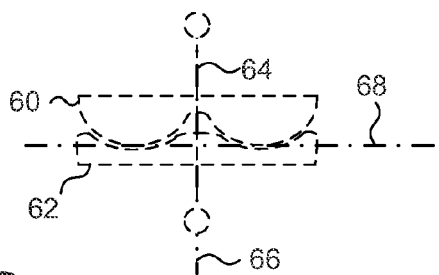
Figure 8D:
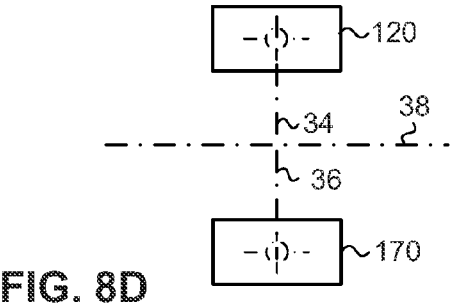

FIGS. 7B and 8B illustrate images 60 and 62 and support bodies 120 and 170 after making adjustment C to the position of support body 210. Thus, images 60 and 62 are shown parallel to each other and support bodies 12 and 170 are also shown parallel to each other. FIGS. 7C and 8C illustrate the positions of images 60 and 62 after making adjustments Af and At to the positions of support bodies 120 and 170 to bring them into alignment with axial lines 34 and 36. FIGS. 7D and 8D illustrate the positions of images 60 and 62 after making adjustments Bf and Bt to the positions of support bodies 120 and 170 to set the distances between the cut planes and the joint line.

Figure 9:
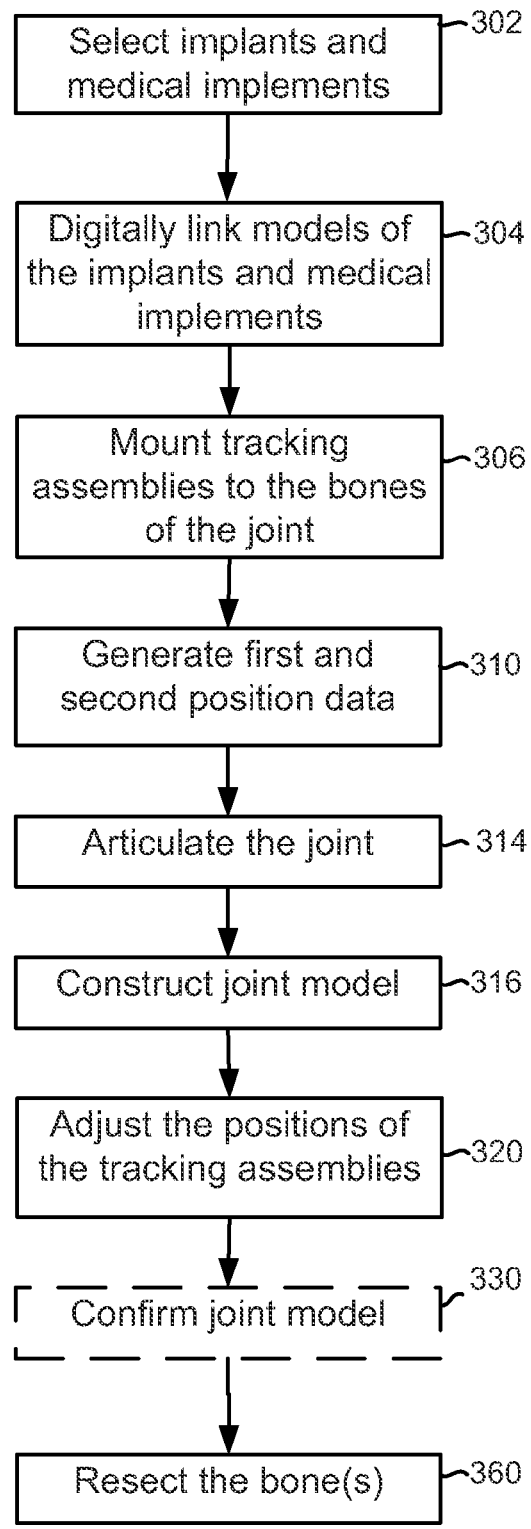
FIG. 9 is a block diagram of an exemplary embodiment of a resection method.

Referring to FIG. 9, one embodiment of a virtual placement method is described therein operable with the system described with reference to FIGS. 3 and 4. In this exemplary embodiment, implants and medical implements are selected as represented by block 302. Implants and medical implements may be selected from the objects catalogue described with reference to FIG. 4 or may be selected in any other manner and the choice provided to the modelling system. As represented by block 304, the models corresponding to the selected objects are digitally linked to other models and to the positions of the tracking assemblies such that as the tracking assemblies move they cause the models to move. Linking allows the modelling software to determine the position of the cut planes based on the dimensions of the implants and to determine the geometric parameters and distances between the support bodies or tracking assemblies and the cut guides. For example, if the support body includes a guide surface, the distance between the predetermined point in the tracking assembly and the cut guide is defined by the selection of the support device. If a separate cut block is attachable to the support body, the distance is predetermined upon the selection of the support device and the cut guide. In an alternative embodiment described further below, where a stabilized resection tool is used to resect the bone, selection of the medical implement causes the processing system to calculate the desired position of the stabilized resection tool and its operating (or safety) envelope. If all the medical implements have corresponding models in the catalogue, linking occurs automatically. Otherwise, the spatial relationship between an un-catalogued implement and the others or the coordinate system employed by the processing system has to be provided.

The selected implements comprising the tracking assemblies are mounted to the bones of the joint as represented by block 306. As shown in FIGS. 3 and 4, a first tracking assembly is supported by a first support device and a second tracking assembly is supported by a second support device. In other embodiments, tracking assemblies may be supported by support bodies that are mounted on the bones without support bases. Affixing the first support device mounts the first tracking assembly to the first bone. From then on, adjusting the first adjustment mechanism of the first support device changes the position of the first support body relative to the first bone and the first support base. The position of the first tracking assembly is tracked by the processing system. As the first bone moves, the position of the first tracking assembly changes. The second tracking assembly may be mounted with the second support device in a similar manner to enable the processing system to track the movement of the second bone and the second support body. The first and second tracking assemblies may be mounted in any order and may be mounted before or after the models are selected and linked to other models.

After the tracking assemblies are mounted, the processing system generates first and second position data corresponding to the first and second positions of the first and second tracking assemblies as represented by block 310. Position data may be generated by the signals processor and then transmitted to the instructions processor. Alternatively, the signals processor may communicate position signals and the storage device may comprise processing instructions to transform position signals to position data. Such transformation may include filtering, sampling, digitization, and calibration of the position data based on the geometry of the tracking assembly and the support body. For example, the signals may be transformed to orthogonalize the raw data with a coordinate system of the tracking assembly. In the case in which more than one tracking technology is used, generation of the first and second position data may include selecting one of the technologies for a selected time period and selecting another technology for other time periods. Drift compensation may also be required to compensate for inertial sensor drift. Position data is generated while the joint is articulated and may be generated continuously.

The joint is articulated as represented by block 314. While the joint and various motions relating thereto are described herein with reference to a knee joint, the implant placement system and method described herein are not limited to any joint and may be implemented in any joint such as hip and shoulder joints. As the joint is articulated, the first and second position data are updated and the virtual joint is presented again with the viewing device. In one motion, the knee is moved from flexion to extension to identify a motion constraint of the knee such as maximum flexion or maximum extension. In another motion, the femur is rotated by oscillating the tibia back and forth to identify the mechanical axis of the femur. In an alternative embodiment, motion of the knee may be restricted by selecting a maximum flexion or extension or inputting a maximum flexion or extension value. Other restrictions may be input as well. The motion of each bone has six degrees of freedom so altogether twelve degrees of freedom may be characterized. As additional motions are performed (or restrictions input or selected) which generate additional constraints, it becomes computationally easier to find the desired axial parameters of the joint.

A joint model is constructed as represented by block 316. In one embodiment, described further below, a search algorithm calculates permutations of two matrices representative of the motions of the first and second models to find the permutation that yields the smallest error in computed joint parameters. Exemplary joint parameters of the knee were described with reference to FIGS. 5 and 6 may include joint lines, gaps, angles, and landmarks. At this point the processing system knows the positions of the tracking assemblies and the geometric relationships between the tracking assemblies and the first and second implants but does not know the relationships between the first and second implants and the axial lines of the joint. The processing system may also know a number of additional motion constraints. For example, the processing system may be programmed with maximum gap distances between the articulating surfaces and to ignore joint models in which the first and second models overlap. Motion constraints may also be input by the surgeon as described above. In some embodiments, soft tissue balance information is obtained qualitatively by the surgeon and/or quantitatively by strain gages and other sensors and the soft tissue balance information is used to further constrain the model. Any permutation that permits motions contrary to the constraints can be automatically ignored. Once a permutation is selected, the relationship between the selected joint parameter and the implants can be determined and the adjustment parameters computed to align the implants. The models may show graphically the necessary adjustments. Adjustment instructions may also be provided with the viewing device along with descriptive information, color-coded symbols, vertical and horizontal gages, and other known means to quickly inform the surgeon.

In an alternative embodiment, the surgeon may iteratively direct the modelling software to change the position of the virtual axial lines relative to the models until the models reflect virtual joint parameters equivalent to the real joint parameters observed by the surgeon. The modelling software may present an image of the virtual joint including the first and second models and the virtual axial lines. Presentation may occur with any suitable viewing device. Exemplary viewing devices include a computer monitor or screen, a glass surface, e.g. a teleprompter, heads-up display, viewing glasses, and the like. Presentation may also comprise projection on a projection surface. The relationship between the models is known based on the relationships of the medical implements and implants. Thus, the surgeon may input up to six degrees of freedom choices to move the virtual axial lines. The surgeon can articulate the knee after each adjustment to validate the previous adjustment and determine a new one.

In another alternative embodiment, upon sensing the image on the viewing device the surgeon may iteratively change the positions of the models by adjusting the adjustment mechanisms of the support devices. In an embodiment where only the first support device is used and the second tracking assembly is stationary relative to a bone, the first model may be changed by adjusting the position of the first support body and the second model, representing a bone that is not to be resected, may be repositioned with the GUI by providing the modelling software with translation or rotation parameters, e.g. entering numbers, selecting a position from a graphical object such as a bar or dial, moving a bar or dial, and the like.

In a further alternative embodiment, the processing system identifies from the first and second position data the translations and rotations of the first and second bone. Comparing the motions to a plurality of known types of motions, the processing system identifies a type of motion and the constraints of such motion. For example, the processing system may subtract first and second motion data and conclude from the results that a flexion/extension motion was performed. From the motion type, the processing system may also extrapolate the range of flexion and extension of the joint. In another motion, where the tibia is rotated during extension, the processing system may extract the rotation range of the tibia. The knee may also be moved in the medial/lateral plane to define another motion constraint.

The positions of the tracking assemblies may be adjusted as represented by block 320. Of course, only one tracking assembly may be articulated if the second tracking assembly is stationary relative to the bone on which it is mounted. The positions of the tracking assemblies may not need to be adjusted in embodiments in which the surgeon iteratively adjusted the positions to construct the joint model. Also, the positions may not need to be adjusted if a stabilized resection tool will be utilized since positioning instructions are utilized instead to control its position.

In one embodiment, the joint model is confirmed as represented by block 330. Confirmation may be performed by articulating the joint after the final adjustments have been made and visually comparing the real joint and the virtual joint.

After confirmation, surgery proceeds as represented by block 360. The surgeon may attach cut blocks and other selected medical implements to the support bodies to position the cut guides and resect the bones. After resection, outriggers and other medical implements may be used to make chamfer and other cuts based on the resections. An outrigger component may also be used to drill holes which receive mounting posts of the implants.

According to another embodiment of the virtual placement system, the system may receive soft tissue feedback to determine, as the joint is articulated, improvements in soft tissue balance. Soft tissue feedback may comprise tension parameters of ligaments and other soft tissue obtained with instrumentation, as well as discrete feedback provided by a user such as qualitative descriptions, e.g. loose, tight, too loose, too tight, and the like, which may be input via voice commands, keyboard, mouse and any other user interface. Based upon soft tissue feedback and position data, the system may compute adjustment parameters for changing the position of at least one of the first and second support bodies to improve soft tissue balance.

According to a further embodiment of the virtual placement system, the modelling software is configured to receive a user input and adjust virtually, based on the user input, the position of the second model relative to a reference device. The second model may represent the articulation surface of the second bone rather than an implant; therefore, rather than physically moving the reference device, a user may change the position of the second model virtually by, for example, using GUI 222 to instruct modelling software 220 to translate or rotate the model. The surgeon observes the physical joint and correlates the relationship between the first and second bones to the virtual joint. When the articulation of the physical joint corresponds with the virtual joint, then the virtual position of the second model is appropriate and the surgeon can proceed to adjust the physical position of the first support body to design a desirable joint. The actual and virtual joint correspond when the virtual joint displayed in the viewing device simulates the motions of the actual joint over the articulation of the joint. Joint articulation may provide the necessary modelling constraints to match the physical to the virtual joint. Alternatively, additional sensors may be provided to establish a spatial relationship between a joint parameter and the bones. Exemplary sensors include track pointers and imaging systems (e.g. cameras and image processing software).

Having described exemplary embodiments of the virtual placement method and system, a more detailed example of a modelling sequence will now be described with reference to an optical tracking system. The tracking assembly includes a bar connecting the support base to a tracker comprising fiducials detectable by an optical camera. In this example, the implant positions are computed relative to the femur and tibia after first mounting tracking assemblies on the femur and tibia. Both bones are then rotated in space relative to their respective mechanical axes, with the femur being rotated by holding the knee still while swinging the tibia back and forth while the joint is in flexion, and the tibia being rotated by placing the foot on the table and then holding the medial and lateral condyles and moving them back and forth in opposite directions. The joint is then articulated from full extension to full flexion by placing the foot in a boot that has a squared heel with a component that fits in and moves along a track. The boot keeps the ankle in dorsiflexion to lock the tibial rotation and may include an inflatable bladder to increase stability of the foot relative to the boot. The boot is then moved back and forth along the track, possibly while holding the femur upright in order to maintain the joint in tension throughout the motion, thereby maintaining the gap between the bones relative to the soft tissue. For deformed joints, or joints with significant flexion contracture due to posterior osteophytes, preplanned soft tissue adjustments may be made, or the osteophytes may be removed, prior to performing the described joint articulation in order for the joint to move during this procedure in the final desired articulation pattern. In another motion, the knee is flexed while in extension in varus-valgus direction to determine ligament laxity which may be used to provide bounds (as opposed to full constraints) on that motion. During each of the described phases of articulation, position data is obtained such that the motion of the tracking assemblies can be virtually played back during the computational phase of the algorithm.

In one such computational phase, the plane normal to the mechanical axis of each bone is determined via the motion of the tracker on that bone during the described rotation by first defining a sphere in the tracker coordinate space about the tracker origin with a radius of, for example, twice the length of the bar that attaches the tracker to the support body, and then locating the two points in the tracker coordinate space that remain stationary within the optical camera coordinate space as the defined sphere rotates within the camera coordinate space in conjunction with the tracker. A regression technique would likely be used to find the best fit points given an imperfect rotational motion in practice. The normal plane relative to the line between these two points can then be computed within the tracker coordinate system. The given implant geometry for the femoral and tibial implants, inclusive of a nominal poly spacer geometry on the tibial implant, can then be located within their respective tracker coordinate spaces in positions that are constrained by the mechanical axis normal planes, and arbitrarily positioned within the remaining degrees of freedom, or possibly positioned using rough estimates of how the bone is oriented relative to the tracker, given the surgical workflow, as an initial guess. For the femoral component, the distal cut plane of the implant would be constrained in the two non-rotational orientations, leaving four degrees of freedom unconstrained, and for the tibia, the proximal cut plane of the implant would be constrained only to maintain the varus-valgus axis of the implant in the normal plane, thereby leaving five degrees of freedom unconstrained, including the flexion-extension orientation of the proximal cut plane. The constraints could also be set to account for surgeon preference or a pre-surgical plan, such as by defining a desired varus tilt to the femoral cut plane relative to the implant coordinate frame, or by constraining the tibial cut plane in the flexion-extension orientation as well, thereby further reducing the unconstrained degrees of freedom. The constraints could be set with known hardware interfaces. For example, constraints could be provided to a processing device with via a keyboard, GUI, mouse, touch screen, and storage device storing the constraints. Constraints could then be listed in a viewing device to facilitate selection of predefined constraints.

An eight or nine degree of freedom optimization problem would then be solved based on the position data collected when the leg was articulated from flexion to extension in order to determine where, within their respective coordinate systems, the implants should be located in order for the components to articulate optimally relative to each other when the joint moves in soft tissue balance. The bones can then be correctly cut to accomplish these implant placements without additional information about the bones themselves, except as noted in several possibilities indicated below. One way to solve this optimization problem would be to define a nine component vector space, in the case of a nine degree of freedom problem, and then use a goodness-of-fit function to find the solution that optimizes the goodness-of-fit function across all relative tracking assembly positions during the articulation.

More generally, a cut plane can be determined by optimizing a virtual joint. The virtual joint is optimized by defining the components of the virtual joint, arranging the components in many different ways, articulating the many arrangements of components, and then selecting the arrangement that most closely simulates the actual joint. The components may comprise models of the bones and implants, and a virtual relationship between the models of the bones. Each arrangement of components is referred to as a permutation of the virtual joint. Each permutation is mathematically articulated, and goodness-of-fit scores are computed for each permutation. The permutation with the optimal score defines the optimal arrangement and is used to define the cut plane. Optimization can be constrained and unconstrained. Unconstrained optimization simulates a perfect joint, a joint without physical constraints. Constrained optimization takes into account constraints, whether based on surgeon preferences or kinematically determined by articulating the joint. The optimization algorithm can account for constraints in several ways. For example, the optimization algorithm can change how the best permutation is selected. In one embodiment, the optimization algorithm weighs the goodness-of-fit function to reward permutations that reflect the constraints. The optimization algorithm can also change how the virtual joint is articulated. In one embodiment, the optimization algorithm constrains the virtual joint so that the optimization space is constrained.

The virtual joint can be constructed with mathematical representations of its components such as matrices and vectors although other mathematical expressions may also be used. Matrices and vectors will be used to describe the optimization algorithm in unconstraint and constrained modelling examples for convenience. In the unconstrained modelling example, two matrices are defined, and the matrices are converted to vectors, each having six variables. Thus, a set of twelve variable values mathematically defines the virtual joint. The vectors are then articulated and the goodness-of-fit function evaluated to determine a goodness-of-fit score. In the constrained modelling example, some of values are determined (e.g. constrained) by the values of other variables. For example, the value of one variable could be defined as being ½ of the value of another variable. When the matrix is converted, the number of vector variables is thus reduced by the number of constraints. A constraint could bind several cells. As the number of constraints increase, it becomes computationally cheaper to optimize the goodness-of-fit function.

The goodness-of-fit function characterizes a relationship between two three-dimensional spatial surfaces determined by a set of values of the mathematical representations of the bone positions (e.g. matrix values). The goodness-of-fit function is evaluated with a plurality of sets of values that permutate the relationship between the mathematical representations of the bones. The optimal permutation is used to determine the cut planes of the bones to form the new joint. The optimal permutation is found by articulating the virtual joint according to each set of permutation values, generating goodness-of-fit scores for each permutation, and finding the permutation that yields an optimal score. A score for a given permutation indicates how well the two surfaces fit together over the articulation range of the joint. A different permutation changes the relationship between the two surfaces so the score for that permutation will indicate a different degree of fit. In one embodiment, the goodness-of-fit function could comprise the sum of the shortest distances between points on one surface and the other surface. For example, one potential goodness-of-fit function would be the sum of the minimum distances between the medial and lateral condylar surfaces on the femoral component and their respective compartment surfaces on the tibial component. Additional minimum distances would be obtained as the joint is mathematically articulated. The score for this goodness-of-fit function would be the sum of the shortest distances, and the optimal score would be the lowest score. In another embodiment, the function could comprise integration of the distance between the two surfaces over the area of both surfaces. Again, the lowest score would be the optimal score.

In a further embodiment, in which an ideal relationship between the two surfaces has been predetermined based on the selection of the implants and/or bone dimensions, the goodness-of-fit function comprises the maximum error computed during mathematical articulation. To compute the error, the distances between the surfaces would be compared to the distances predicted according to the ideal relationship. The sum of all the errors obtained during mathematical articulation represents the maximum error. The permutation that yields the minimum maximum error determines the optimal fit between the implants. Other known computational techniques may also be used to define goodness-of-fit functions.

As describe previously, the goodness-of-fit function may be weighed to penalize the permutation when the virtual surfaces articulate in manner that is inconsistent with motion constraints of the actual patient joint. In one embodiment, the function is weighed to penalize the score when the virtual surfaces overlap more than a tolerance amount. For example, the score could be set to infinity when the virtual surfaces overlap more than the tolerance amount ensuring that the particular permutation will not be chosen. In another embodiment, the function could be weighted more heavily medial than lateral, which could reduce the likelihood of overstuffing the lateral compartment. In a further embodiment, the function could be modified by the positions of the implants relative to additional landmarks collected by the surgeon with a separately tracked pointer to enforce additional desired constraints, such as by greatly increasing the score if the anterior cut surface of the femoral implant is placed posterior to an anterior surface landmark position, which would be indicative of a potential femoral notching situation. In yet another embodiment, the function could be weighed by increasing the score by an amount relative to the distance from the sagittal plane of the tibial implant through its midline and the intercondylar eminence point, thereby translationally constraining the solution along the joint line. In another embodiment, a third tracking assembly could be placed on the patella, and the patellar position could also be tracked during the joint articulation. The goodness-of-fit function could be further modified to account for how well the trochlear groove of the femoral component tracks the natural patellar-femoral joint line, for example. Although the above embodiments are described with reference to a knee joint, goodness-of-fit functions for hip and shoulder joints can be analogoulsy weighed.

As indicated above, a plurality of permutations are defined to test for the optimal solution. The permutations are arbitrarily defined. For example, the boundaries of the vector space may be initially chosen. Additional permutations could be selected at regular intervals between the boundaries. In one embodiment, permutations are arbitrarily defined and tested until the score falls within a predetermined acceptable range. An error may be indicated if the score fails to fall within an acceptable range in a given amount of time. In another embodiment, a number of permutations are tested to find a good solution, and the good solution is then used as a seed to test additional permutations in an evolutionary manner. For example, a first predetermined number of permutations may be used to test the boundaries of the vector space. A second predetermined number of permutations may the be defined around the good solution (e.g., the solution with the minimum maximum error or the solution with the smallest sum of distances, or any solution satisfying the optimization criteria for a particular goodness-of-fit function). The intervals between the permutations in the second set may be narrower than in the first set. The evolutionary process is continued until a sufficiently good or bad score is obtained at which time the process ends. In a further embodiment, multiple permutations may be initiated, and after a seed permutation is selected from a first set, multiple sets may be defined based on the seed. In this manner, a plurality of sets of permutations are tested in each cycle which may result in a faster overall process of convergence.

Upon achieving a successful solution, the implant geometries could be virtually articulated within the camera coordinate system to allow visual confirmation of the plan. Atlas bone models could be used in conjunction with the implant geometries as a visualization aid for the surgeon to review the planned implant geometry articulation in a rendered view, which may include both three orthogonal views, including one normal to the joint line, for example, as well as a 3D surface display that can be arbitrarily reoriented via the user interface. Additionally, if a 3D patient specific data set is available, such as a CT or an MRI scan, where segmented bone models have been generated that includes planar and other landmarks which correspond to those identified intraoperatively as described above, these models may be used to provide a true post-surgical kinematic simulation for the patient after virtually placing the implants on the bones relative to the given landmarks.

The surgeon could then review the plan relative to the actual patient anatomy. For example, a tracked pointer with a planar surface could be used by the surgeon to inspect the planned primary resection surface positions relative to the actual patient bones. The surgeon would then have the opportunity to adjust the plan constraints or change the implant geometry and to regenerate the solution to account for the changes. The surgeon could determine, for example, that a larger implant size or a thicker poly spacer should be used if indicated resection levels are not deep enough on either bone. The software could also indicate to the surgeon that a different implant size should be considered based on an analysis of the solution. For example, if the minimum surface distance tends to widen, in the optimal solution, as the joint articulates into flexion, this may indicate that a larger implant size may be appropriate, which could be suggested by the software. The interface with the surgeon could be based on tracked hand gestures, a bagged iPod Touch™ distributed by Apple, Inc., other touch screen mechanisms located on the surgeon's arm, verbal commands to a nurse to modify parameters using a keyboard, voice recognition, or any other suitable communication interface.

Once an acceptable plan has been generated, any instrumentation system that can integrate with the optical tracking system can be used to execute the plan, including existing CAS solutions or novel solutions specifically developed to take advantage of the unique characteristics of the described planning technique. Exemplary instrumentation systems are described with reference to FIGS. 3, 4, 13, 14, 16 and 19. Another such instrumentation system may include a tracked articulating saw that automatically positions and holds a saw blade in one or more of the defined bone cut planes independent of the surgeon hand motion, thereby alleviating the need for any instrumentation, such as cut guides and alignment jigs, other than saw and the tracking assemblies, to perform the procedure. An example of such an instrumentation system is described with reference to FIGS. 14 and 15. Advantages to this approach include surgical workflow simplification, instrument reduction, and reduced operating room time relative to the use of traditional or existing CAS instrumentation sets. Improved planning consistency relative to soft tissue balance could also reduce soft tissue releases to achieve adequate balance and improve patient outcomes via a more natural feeling knee and reduced chance of revision or early wear.

Figure 11:
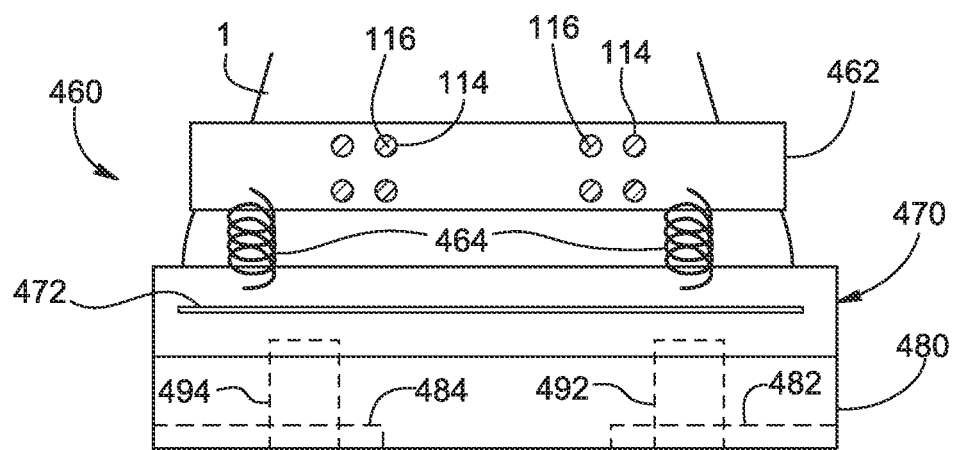
FIG. 11 is an elevation anterior view of an outrigger component attached to a distal cut guide which is adjustably coupled to a femur.

Referring now to FIG. 10, a perspective view of an embodiment of a support device, denoted by numeral 400, is shown. Support device 400 comprises a support base 402 adjustably coupled by an adjustment mechanism 404 to a support body 442. Generally, multidimensional adjustment mechanisms comprise slots slidably receiving dovetailed rails, screwgears for converting rotational motion into linear motion, hinged walls, gimbals, universal joints and apertures for receiving pins, posts and other attachment members. In the embodiment depicted in FIG. 10, the adjustment mechanism includes a platform 426 slidably coupled to support base 402 by a slot 424. A screw 422 rotates to translate platform 426 and a support block 442, which is supported by platform 426, parallel to the longitudinal axis of slot 424. Support body 442 is coupled to platform 426 by a hinge wall 440 and a second hinge wall (not shown). Hinge wall 440 may be resiliently flexed by a screw 438 to rotate (pivot) support body 442. Similarly, the second hinged wall may be flexed by a screw 428. In combination, screws 422, 428 and 438 provide one translational and two rotational adjustments. Any surface of support body 442 may be designated as a reference surface, e.g. surface 450, 452, 454. Apertures (not shown) configured to receive attachment members may be provided in surfaces 450, 452, 454 to attach a surgical implement thereto as shown in FIG. 11. Exemplary embodiments of multidimensional adjustment mechanisms which may be configured as support devices to adjustably couple a surgical implement to a bone are disclosed in U.S. Pat. No. 7,520,800 and U.S. Pat. Publ. Nos. 2006/0293681, 2006/0200158, 2007/0005073, 2008/0140081 and 2008/0065085 which are commonly owned and are incorporated by reference herein in their entirety. In another embodiment, the support body may be adjusted by translation in one or more of three directions and rotation in one or more of three directions. In a further embodiment, the support body may be moved with six degrees of freedom.

Figure 12:
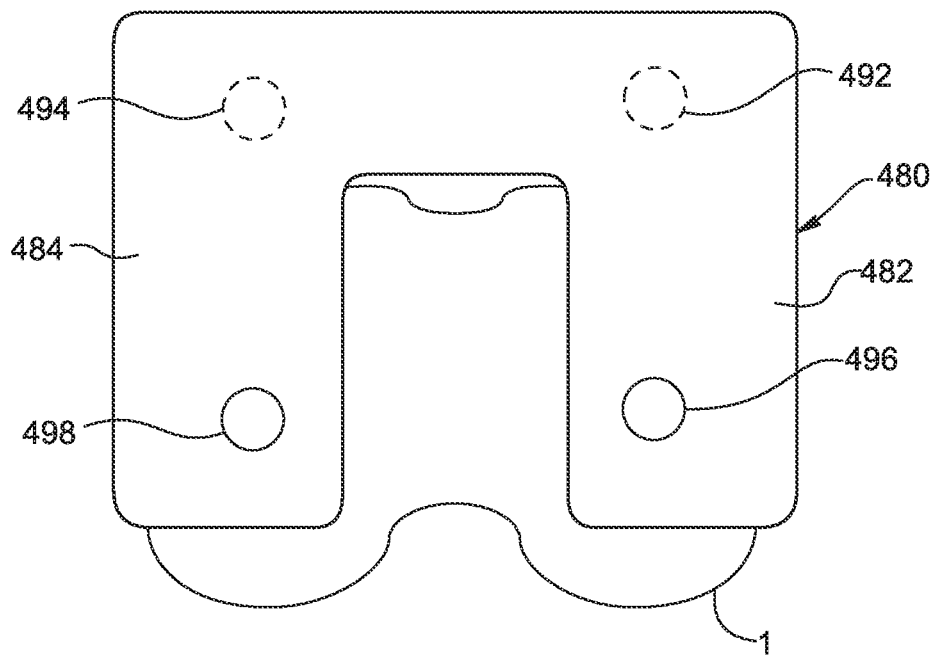
FIG. 12 is a plan distal view of the outrigger component and the femur shown in FIG. 11.

FIGS. 11 and 12 are anterior and distal conceptual views of bone 1 showing a support device 460 and an outrigger component 480. Support device 460 is mounted onto bone 1 and secured thereto by support members 116 which are received by apertures 114 in a support base 462. An adjustment mechanism is represented conceptually by members 464 adjustably coupling support base 462 to a combo cut guide 470. Combo cut guide 470 comprises a support body incorporated with a cut guide 472 provided for guiding a cutting instrument therethrough. Also included is a tracking assembly (not shown) to track the position of cut guide 472. In alternative embodiments depicted in FIG. 19, support devices support cut guides 662 and 674. Outrigger component 480 is detachably coupled to a reference surface of combo cut guide 470 in a predetermined geometric relation by components passing through apertures 492 and 494 and includes feet 482 and 484. Additional surgical components may be attached to combo cut guide 470 to perform additional resections. Feet 482 and 484 include guide holes 496 and 498 which guide a drill therethrough to perforate bone 1. Mounting posts of an implant may be positioned in the perforations. Advantageously, combo cut guide 470 enables alignment of cut guide 472 with a desired cut plane to resection bone 1 and perforation of bone 1 based on the placement of combo cut guide 470 to guide placement of the implant or other resectioning tools on bone 1.

A number of alternative embodiments of a virtual placement system may be implemented to take advantage of different medical implements such the adjustable cut block described with reference to FIG. 10, the combination cut block described with reference to FIGS. 11 and 12, a stabilized resection tool described with reference to FIGS. 14 and 15, a remotely aligned cut block described with reference to FIGS. 16-18, and viewing screens described with reference to FIGS. 20 and 21.

Figure 13:
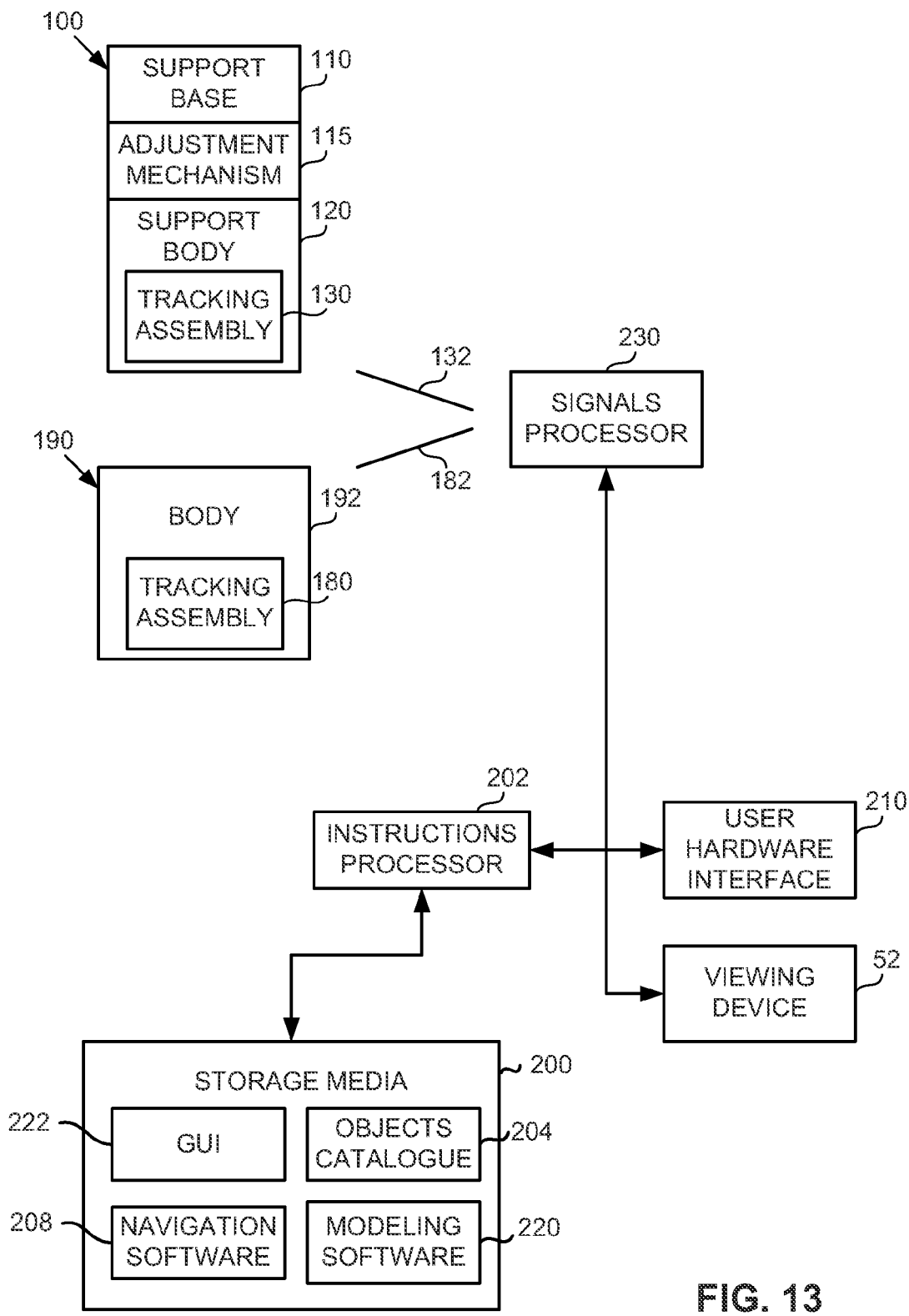
FIG. 13 is a block diagram of another embodiment of the positioning system comprising a support device as shown in FIG. 4 and a trackable reference device.

Referring now to FIG. 13, another embodiment of the system is disclosed. The embodiment depicted in FIG. 13 is similar to the embodiment depicted in FIGS. 3 and 4 except that support device 150 has been replaced with a reference device 190 comprising a body 192 supporting tracking assembly 180. Reference device 190 is mounted on a bone. The bone may be resected according to the method disclosed with reference to FIG. 9. In an alternative embodiment, the bone on which support device 100 is mounted is resected while the other bone of the joint, onto which reference device 190 is mounted, is not resected. In said embodiment, tracking assemblies 130 and 180 are used to characterize the joint and define a cut plane with reference to support body 120 as described above.

Figure 14:
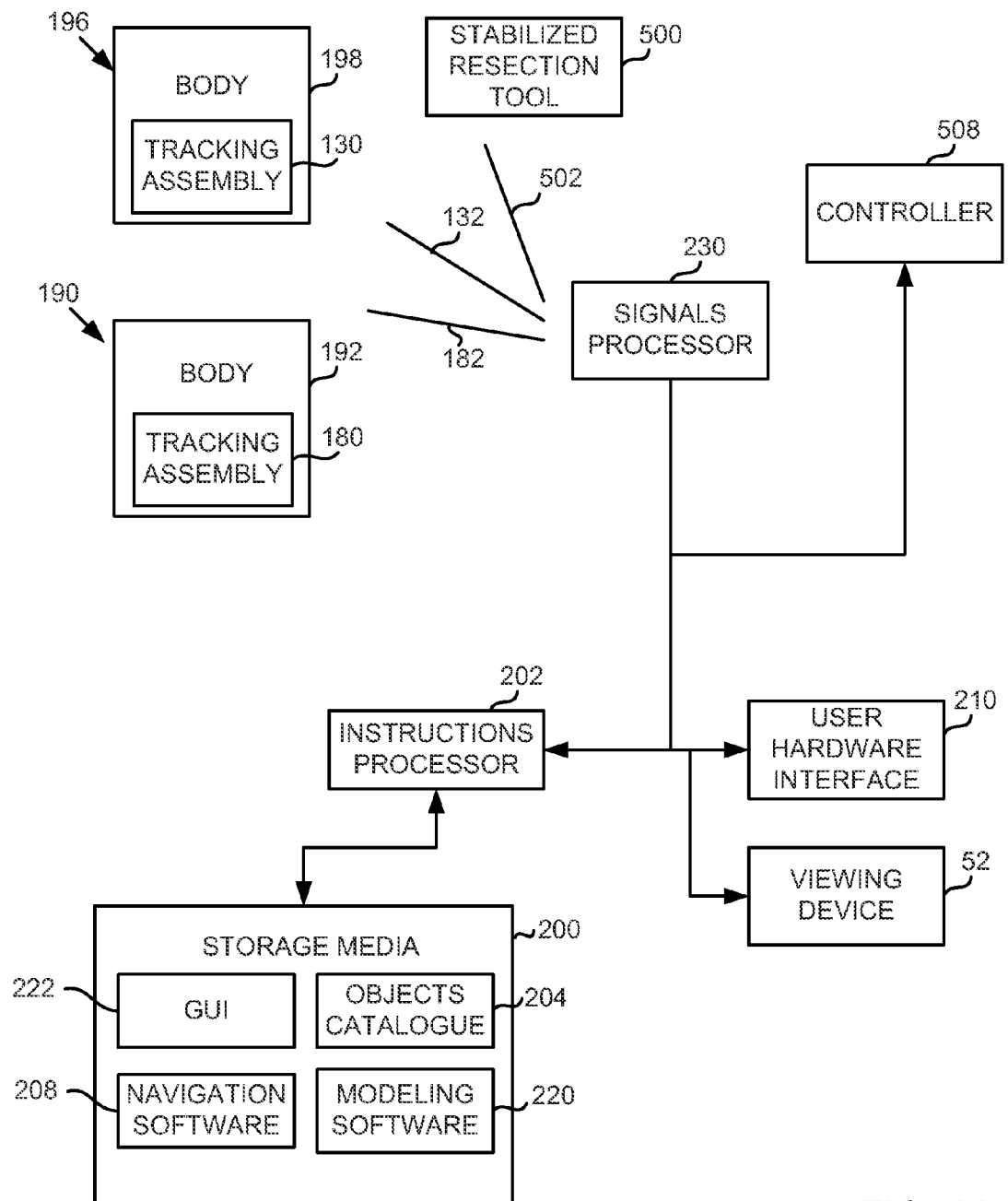
FIG. 14 is a block diagram of another embodiment of the positioning system comprising a trackable reference device as shown in FIG. 4, a second trackable reference, and a stabilized resection tool.
Figure 15:
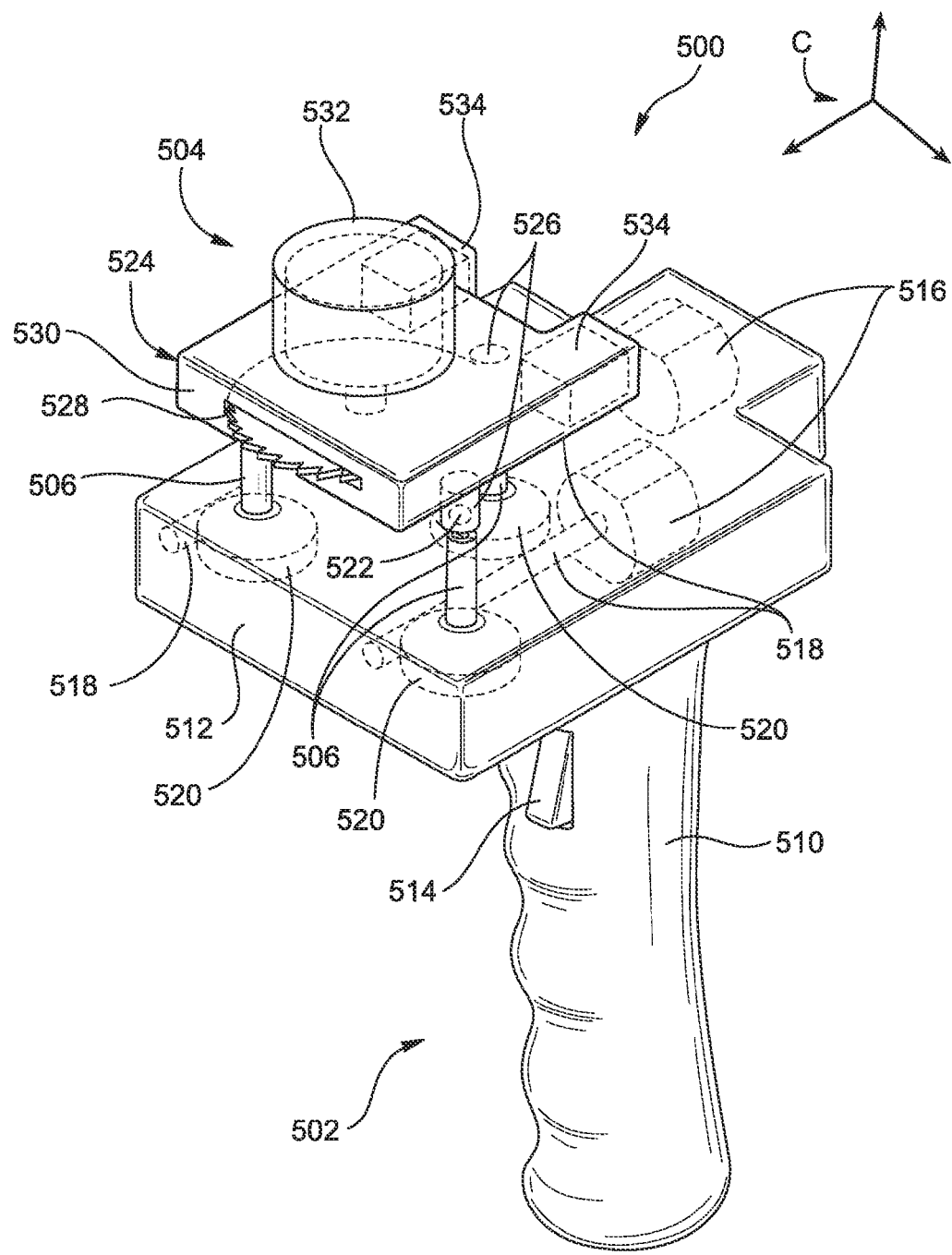
FIG. 15 is a perspective view of a stabilized resection tool operable with the positioning system of FIG. 14.

FIGS. 14 and 15 disclose yet another embodiment of the virtual placement system. The embodiment depicted in FIG. 14 is similar to the embodiment depicted in FIG. 13 except that support device 100 has been replaced with a reference device 196 comprising a body 198 supporting tracking assembly 130. Additionally, an automatically stabilized bone resection tool and components operable to control the operation of the resection tool are also disclosed with reference to FIGS. 14 and 15. Exemplary automatically stabilized bone resection tools are disclosed in U.S. Patent Application No. 61/318,537 entitled AUTOMATICALLY STABILIZED BONE RESECTION TOOL filed on Mar. 29, 2010, the entire disclosure of which is expressly incorporated by reference herein. As disclosed therein, an automatically stabilized bone resection tool, denoted in FIGS. 14 and 15 by number 500, allows a surgeon to perform a guided resection in a "free hand" manner by preserving a desired position a resection body 524 of resection tool 500 with respect to a bone, irrespective of movement of the tool's operator interface. Resection tool 500 includes a resector assembly 504 comprising resector body 524. Resector assembly 504 is connected to an interface base 512 of an operator interface 502 by a plurality of actuators 506 which are actuated by worm drives 518 and worm gears 520, driven by motors 516, as required to maintain a desired position of resector body 524 during "free hand" movements of operator interface 502. Exemplary linear actuators are shown although any actuation mechanism capable of raising, lowering, and changing the orientation of resector body 524 relative to interface handle 510 may be used, such as hydraulic, pneumatic, and other mechanical systems. A plurality of ball joints 522 support resector body 524 at a plurality of attachment points 526. Resector body 524 comprises a surface 530 through which a blade 528 extends to resect the bone. Blade 528 is driven by a cutting motor 532. A tracking assembly 534, similar to tracking assemblies 130 and 180, cooperates with signal processor 230 to generate signals 502 representing the position of resector body 524.

Operator interface 502 includes an interface handle 510 supporting interface base 512. Interface handle 510 includes a trigger 514 for activating motor 532 to rotate blade 528. Although a circular saw blade is shown, it is within the scope of the present disclosure that blade 528 may be any suitable cutting instrument, such as a reciprocating blade, scalpel, particulate stream, retractable blade, laser and the like. It is also contemplated that other controls may be placed on interface handle 510, such as manual override switches for actuators 506, a power switch, status indicator lights for displays, toggle switches for toggling between cut modes, and the like. Further, it is contemplated that trigger 514 and/or other manual switches may be eliminated entirely. A controller 508 is operably coupled, hardwired or wirelessly, to resection tool 500 to control at least partially operation of resector assembly 504 according to predetermined instructions programmed into controller 508 or navigation software 208. Controller 508 may comprise PID feedback processors, servo-motor controllers and other electronic components configured to accurately control the operation of actuators 506 and position of resector body 504. Sensors (not shown) may provide feedback to controller 508 to improve stabilization of resector body 524. Bone resection tool 500 may be navigated with navigation software 208 based on position signals 502 to the desired cut planes. Viewing device 52, user hardware interface 210, and GUI 222 may be utilized to instruct the surgeon on how to bring resection tool 500 near a desired resection plane and within the control range of actuators 506. Navigation software 208 may be programmed to shut-off operation of blade 528 when the position of resector body 524 approaches the control limits of actuators 506.

Figure 16:
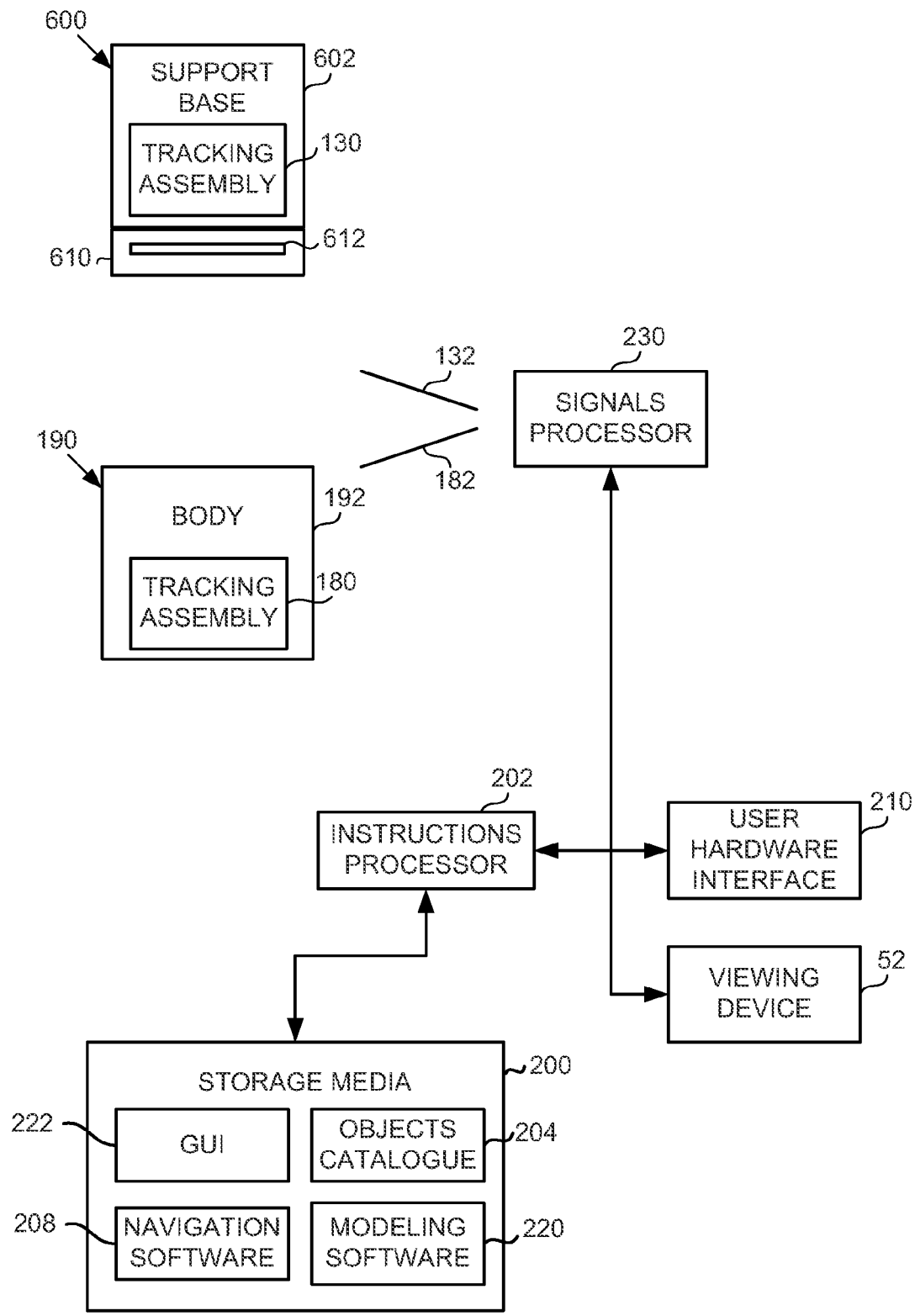
FIG. 16 is a block diagram of a further embodiment of the positioning system comprising a trackable reference device as shown in FIG. 13 and a trackable support base supporting a cut block.

A further embodiment of the virtual placement system is disclosed with reference to FIGS. 16-18. The embodiment depicted in FIG. 16 is similar to the embodiment depicted in FIG. 13 except that support device 100 has been replaced with a support base 600 comprising housing 602 and tracking assembly 130. Once support base 600 is mounted on a bone, tracking assembly 130 is stationary relative to the bone. Additionally, a remote docking station 630 and a remotely aligned cut block 610 are disclosed with reference to FIGS. 17 and 18. Remotely aligned cut block 610 is shown in FIG. 16 connected to housing 602. Exemplary remote alignment cut blocks and docking stations are disclosed in U.S. patent application Ser. No. 12/207,891 entitled METHOD AND APPARATUS FOR REMOTE ALIGNMENT OF A CUT GUIDE filed on Sep. 10, 2008, the entire disclosure of which is expressly incorporated by reference herein. Referring again to FIG. 16, after mounting, tracking assemblies 130 and 180 are stationary relative to bones 1 and 3. Housing 602 is configured to removably connect with cut block 610.

Referring to FIGS. 17 and 18, remotely aligned cut block 610 is shown docked in remote docking station 630. Cut block 610 comprises a cut guide 612, an adjustment mechanism, and a body 616. Body 616 includes a plurality of apertures 618 which cooperate with apertures (not shown) in docking station 630 to removably secure cut block 610 to docking station 630 and, after adjustment, to removably secure cut block 610 to support base 602. The exemplary adjustment mechanism shown in FIGS. 17 and 18 includes a locking mechanism 614 and adjustment supports 620 and 622 which are adapted to engage adjustment rods 636 of docking station 630. Advantageously, cut block 610 is aligned remotely via remote docking station 630 which reduces the size of cut block 610 by the avoidance of the adjustment mechanism on the cut block. Docking station 630 includes a base 632 and driving mechanisms 634. Driving mechanisms 634 include adjustment rods 636 which are driven by worm gears or other driving means (not shown), manually or automatically, to extend linearly from driving mechanisms 634 to adjust the position of cut block 610 relative to docking station 630. Additional driving mechanisms may be provided to adjust the position of cut block 610 relative to docking station 630 in up to six degrees of freedom. After adjustment, locking mechanism 614 sets the position of cut guide 612 relative to cut block base 616. Locking mechanism 614 may include a ball and socket (not shown) in which the ball extends from cut block 610 and a collet mechanism (not shown) in a socket disposed in base 614 used to selectively lock cut block 610 relative to base 632. Then, cut block base 616 is disconnected from docking station 630 while in the locked position and connected to support base 602. The adjustment mechanism may be constructed and adjusted as described in other embodiments of adjustment mechanisms described herein to align cut guide 612 with a desire cut plane.

Figure 19:
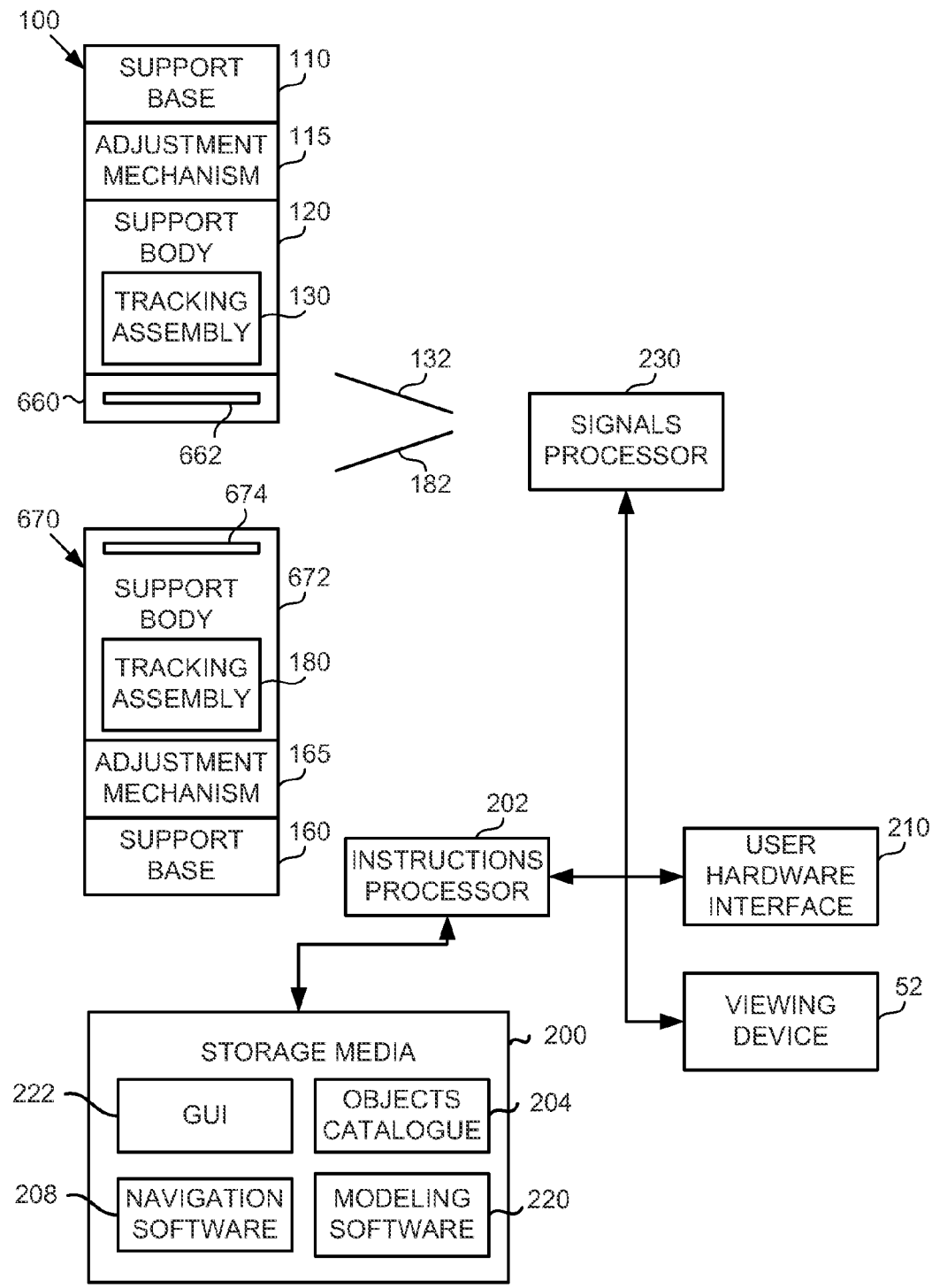
FIG. 19 is a block diagram of a yet further embodiment of the positioning system comprising a support device supporting a cut block and a support device comprising a cut guide.

FIG. 19 illustrates an alternative feature of the embodiment of the virtual placement system described with reference to FIGS. 3 and 4. As disclosed therein, the system includes support device 100 and support device 150. In the present embodiment, a cut block 660, which comprises a cut guide 662, is removably attachable to support device 100. Furthermore, a support device 670 is provided instead of support device 150. Support device 670 is similar to support device 150 except for the addition of a cut guide 674 to support body 672. Thus, the combination of support device 100 and cut block 660, support device 670, enable trackable adjustment of cut guides 660 and 674 relative to the bones on which they are mounted so that cut guides 660 and 674 may be tracked and navigated into alignment with desired cut planes.

Referring now to FIGS. 20 and 21, a viewing system is disclosed operable with a tracking system to assist the surgeon in modelling the joint. Additional embodiments of tracking systems including imaging and display systems are disclosed in U.S. Patent Application No. 61/317,959 entitled COMPACT COMPUTER ASSISTED SURGICAL SYSTEM filed on Mar. 26, 2010, the entire disclosure of which is expressly incorporated by reference herein. The viewing system includes a viewing device 804 suitable for use with tracking systems disclosed therein and herein to adjust the position of support bodies, remotely aligned cut blocks, and automatically stabilized resection tools in the same manner as viewing device 52 may be used. Advantageously, viewing device 804 allows the surgeon to simultaneously view images displayed in viewing device 804 while also observing the joint. Simultaneous viewing is particularly important to observe differences, while the joint is articulated, between characteristics of the joint and of the virtual joint displayed in viewing device 804. Optionally, the system may include a camera 820 arranged to capture images of the joint. Camera 820 may include zooming, night vision, and other common features. Exemplary cameras include optical still and video cameras, infra-red cameras, laser scanning cameras, and any other camera adapted to capture images in any wavelength. Viewing device 804 may include a receiving surface 806 and a display surface 808 suitable for displaying an image 810, illustrating the joint, and/or an image 812, illustrating the virtual joint, and, optionally, a projector 802. Projector 802 projects images 810 and 812 using either a front-projection (FIG. 20) or a rear-projection (FIG. 21) modality. While a knee joint may be articulated with the patella still in place, image 810 represents the joint with the patella removed to facilitate understanding. In an alternative image, the patella may also be displayed and, advantageously, may be displayed in a translucent image.

An exemplary viewing device 804 comprises a translucent flat panel. Embodiments of viewing device 804 in which receiving surface 806 and display surface 808 comprise a single surface (i.e., a front-projection modality) are also contemplated as shown in FIG. 21. In another alternative embodiment, viewing device 804 comprises an opaque surface such as a wall or board. In a further alternative embodiment, viewing device 804 may comprise a flat screen television, a computer touch-screen, or a computer tablet. Images may be provided for display on viewing device 804 by projector 802 or by a computer communicatively coupled to viewing device 804, e.g. wirelessly or hard-wired. Images 810 may be obtained from camera 820 directly or sent from camera 820 to a processing device where images (still or frames captured from a video stream) can be analyzed to extract data therefrom. For example, the articulating surfaces of the joint may be characterized by comparing the gap between the articulating surfaces to the known sizes of the condyles. In this manner, the processing system can generate a digital scaled image of the joint, inclusive measurements, based on known landmarks detectable in the stream of images, and only present on viewing device 804 those features of the joint relevant to the particular step of the resection method being performed (i.e. a "scrubbed" image). As different steps are performed, the processing system can tailor images to those steps. For example, the processing system may display side-by-side on viewing device 804 the virtual joint model, e.g. image 812, and a scrubbed image of the joint, e.g. image 810, in real-time to facilitate comparison of the articulation of the joint to the virtual articulation of the joint model. Camera images may also be processed to identify the bones and joint landmarks from which the position of joint parameters may be determined to construct a joint model. Scrubbed images may be used as well. Additional cameras may be used to obtain stereoscopic views which increase detail. A laser scanner is particularly suitable to determine depth which, without a laser scanner, is extracted from images by triangulation and other known techniques.

Figure 22:
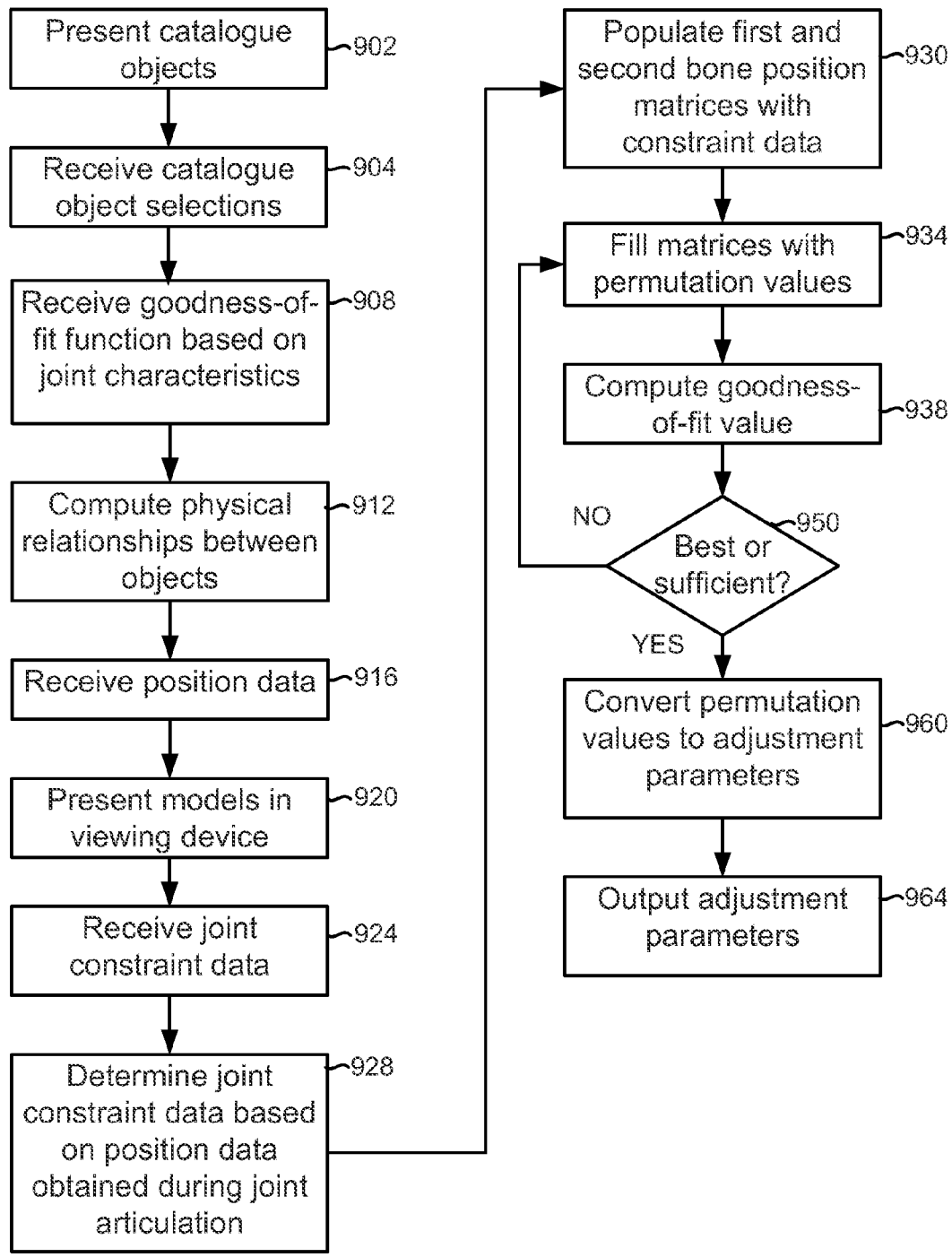
FIG. 22 is a block diagram of an algorithm to kinematically characterize a joint.

Referring now to FIG. 22, an exemplary embodiment of a modelling algorithm adapted to facilitate the virtual placement method will be described. The modelling algorithm will be described with reference to functions performed by the instructions processor in response to processing sequences stored in the storage media. The term "present" means to output images on output device such as a viewing device. Images include text images. The term "receive" means to obtain information, signals or data from a source such as the user hardware interface, the tracking assemblies and the signals processor. Additional data may be received from implements designed to measure soft tissue and from other trackable medical implements.

The algorithm begins with system configuration at 902-912. Catalogue selections are presented at 902 to enable a user to input selections which, at 904, are received by the processing system. The user then loads a goodness-of-fit-function and the function is received by the processing system at 908. The function may be loaded once and reused in multiple surgeries. For example, the function may be scalable according to the size of the joint, in which case the processing system presents a GUI with which a scale may be selected and then received by the processing system. The system could also allow for selection of a standard configuration from a plurality of configurations, and for saving a configuration after surgery as another of the plurality of configurations. In this manner, a surgeon's preferences could be saved and re-loaded for another surgery. At 912, the processing system links objects based on their functions and computes spatial relationships between them. For example, the processing system may calculate the distance from a point in a tracking assembly of a support device to a cut guide supported by the support device or the distance between the engagement surface of an implant to a tracking assembly based on their attachment mechanisms and configurations.

Models are presented at 920. At 924, the processing system may present a GUI to receive joint constraint information from a user. A number of joint constraints may also be associated with the implant models and automatically loaded upon receipt of an implant selection at 904. Patient-specific constraints may be received via the GUI or may be input from a computer file. Constraints may be received during system configuration or at any time during the procedure. For that purpose, the GUI may present an option for a user to select new medical implements. Upon selection of a new medical implement, which may comprise a different implant size, the processing system performs functions 902, 904, 912 and 920 to automatically reconfigure the object relationships.

Joint constraint data is determined at 928. Joint constraint data is determined by comparing position data obtained during articulation of the joint to an unconstrained joint model. Constraints may be validated by presenting a simulation of the range-of-motion of the constrained joint. The surgeon may then be permitted to remove or change constraints using a GUI or a data input table.

Matrix population is performed at 930. The sizes of the matrices depend on the number of degrees of freedom allowed to each bone. Constraints fill some of the cells of the matrices and the remaining cells are filled with arbitrary permutation values at 934.

Once the matrices are filled, a goodness-of-fit value is computed at 938 and, at 950, the value is compared to the previous best value. If the new value is below a predetermined threshold, the fit is sufficiently good. Otherwise, if the value does not converge or improve sufficiently, constraints may need to be changed and the step restarted. If a good fit is found, the permutation values are converted to adjustment parameters at 960 and the adjustment parameters are output at 964. As described previously with reference to adjustment mechanisms, the parameters may be presented with the viewing device to facilitate manual adjustment or transmitted to automatic adjustment mechanisms such as the mechanisms described with reference to FIGS. 17 and 18. The surgeon may also choose to modify the resection plan after the adjustment parameters are calculated. In one embodiment, a display of the leg with the constraint geometry shown for each bone, i.e. a plane normal to the mechanical axis on the femur and a line in varus/valgus on the tibia, is shown on a viewing device. The surgeon could touch a displayed object and get a drop-down of images of different geometric objects that could be used in the given context. Some objects could be shown solid to represent fixed constraints, and some could be shown fuzzy to represent bounding or weighted constraints. The surgeon then could, via GUI objects such as up/down arrows, change any applicable parameters including implants and constrains. The plan would then be recomputed and redisplayed.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A virtual implant placement system for determining a first cut plane to resect a first bone, the first bone and a second bone being part of a joint, the system comprising:
    a first tracking assembly adapted to be supported by the first bone and operable to generate a first position data corresponding to a plurality of first positions of the first tracking assembly as the joint is articulated;
    a second tracking assembly adapted to be supported by the second bone and operable to generate a second position data;
    a first implant model of a first implant, the first implant model linked to the first tracking assembly, the first implant model having at least two versions;
    a second model of one of a second implant and the second bone, the second model linked to the second tracking assembly; and
    a processing device determining the first cut plane by:
        digitally linking at least a first version of the first implant model to the first bone to construct a virtual joint defining a relationship between articulating surfaces of the first implant model and the second model;
        modelling a movement of the virtual joint based on movements of the first bone relative to the second bone based on a tracking of the first and the second tracking assemblies;
        repeating the digitally linking and the modelling with a second version of the first implant model; and
        determining the first cut plane based on a selected version of the first implant model, the first position data, the second model, and the second position data through said movement of the virtual joint; and
    a viewing device displaying data related to the first cut plane.

2. The virtual implant placement system of claim 1, wherein the second position data corresponds to a plurality of second positions of the second tracking assembly as the joint is articulated.

3. The virtual implant placement system of claim 1, wherein the system further comprises a goodness-of-fit function, wherein the processing device performs a plurality of permutations of the virtual joint, for each permutation articulates the virtual joint and computes a goodness-of-fit score, and determines the first cut plane based on the permutation that yields an optimal score.

4. The virtual implant placement system of claim 3, wherein the optimal score is the lowest score.

5. The virtual implant placement system of claim 3, wherein the goodness-of-fit score comprises a maximum goodness-of-fit error, and the optimal score is the minimal maximum goodness-of-fit error.

6. The virtual implant placement system of claim 3, wherein the goodness-of-fit function is weighed to favor permutations that reflect motion constraints of the joint.

7. The virtual implant placement system of claim 6, wherein the motion constraints of the joint are derived from the first position data and the second position data.

8. The virtual implant placement system of claim 6, wherein the motion constraints are provided to the processing device.

9. The virtual implant placement system of claim 6, wherein the motion constraints are selectable from a list presented with a viewing device.

10. The virtual implant placement system of claim 3, wherein the virtual joint is constrained according to motion constraints of the joint.

11. The virtual implant placement system of claim 10, wherein the motion constraints of the joint are derived from the first position data and the second position data.

12. The virtual implant placement system of claim 10, wherein the motion constraints are provided to the processing system.

13. The virtual implant placement system of claim 10, wherein the motion constraints are selectable from a list presented with a viewing device.

14. The virtual implant placement system of claim 1, further comprising a stabilized resection tool including an operator interface, a cutting tool, a plurality of linear actuators rotatably coupling the operator interface and the cutting tool, and a tracking assembly operable to generate a third position data corresponding to the position of the cutting tool, wherein the processing device actuates at least one of the plurality of linear actuators to align the cutting tool with the first cut plane.

15. The virtual implant placement system of claim 1, further comprising a guide surface adapted to guide a cutting tool, wherein the processing device outputs adjustment parameters to align the cutting tool with the first cut plane.

16. The virtual implant placement system of claim 15, further comprising a support base including a plurality of apertures configured to removably affix the support base to the first bone, an adjustment mechanism supported by the support base and including a plurality of linear actuators, the linear actuators supporting the first tracking assembly and the guide surface, the linear actuators actuated according to the adjustment parameters to align the guide surface and the first cut plane.

17. The virtual implant placement system of claim 16, wherein the adjustment parameters are displayed with a viewing device to enable manual actuation of the linear actuators.

18. The virtual implant placement system of claim 16, wherein the adjustment mechanism further includes a plurality of motors operable according to the adjustment parameters to actuate the plurality of linear actuators.

19. The virtual implant placement system of claim 15, further comprising an adjustable cut block and a docking station, the adjustable cut block including a cut block base, the guide surface adjustably coupled to the cut block base, and a locking mechanism, the docking station including at least one driving mechanism for adjusting a position of the guide surface relative to the cut block base according to the adjustment parameters when the adjustable cut block is mounted onto the docking station, the locking mechanism locking the position of the cut block base relative to the guide surface.

20. The virtual implant placement system of claim 19, wherein the adjustment parameters are displayed with a viewing device to enable manual actuation of the driving mechanism.

21. The virtual implant placement system of claim 19, wherein the driving mechanism is automatically actuated according to the adjustment parameters.

22. The virtual implant placement system of claim 1, wherein the processing device also determines a second cut plane adapted to resect the second bone, wherein the first cut plane and the second cut plane are determined independently so as to enable resectioning the first bone and the second bone in any order.

23. The virtual implant placement system of claim 1, wherein the processing device presents the virtual joint in the viewing device including a first visual indication of the first implant model and a second visual indication of the second model, alters the position of the first visual indication relative to the second visual indication in response to movement of the first tracking assembly relative to the first bone, and determines the first cut plane when the virtual joint presented with the viewing device corresponds to the joint through an articulating motion of the joint.

24. The virtual implant placement system of claim 23, wherein the processing device receives an input indicating that the virtual joint corresponds to the joint.

25. The virtual implant placement system of claim 23, further comprising a sensing device to determine a joint landmark relative to the first bone and the second bone, wherein the virtual joint includes a landmark visual indication.

26. The virtual implant placement system of claim 25, wherein the sensing device comprises a trackable pointer.

27. The virtual implant placement system of claim 25, wherein the sensing device comprises a camera generating images of the joint, and the landmark is identifiable in the images generated by the camera.

28. The virtual implant placement system of claim 23, further comprising a stabilized resection tool including an operator interface, a cutting tool, a plurality of linear actuators rotatably coupling the operator interface and the cutting tool, and a tracking assembly operable to generate a third position data corresponding to the position of the cutting tool, wherein the processing device actuates at least one of the plurality of linear actuators to align the cutting tool with the first cut plane.

29. The virtual implant placement system of claim 23, further comprising a guide surface adapted to guide a cutting tool, wherein the processing device outputs adjustment parameters to align the cutting tool with the first cut plane.

30. The virtual implant placement system of claim 29, further comprising a support base including a plurality of apertures configured to removably affix the support base to the first bone, an adjustment mechanism supported by the support base and including a plurality of linear actuators, the linear actuators supporting the first tracking assembly and the guide surface, and the linear actuators actuated according to the adjustment parameters to align the guide surface and the first cut plane.

31. The virtual implant placement system of claim 30, wherein the adjustment parameters are displayed in the viewing device to enable manual actuation of the linear actuators.

32. The virtual implant placement system of claim 30, wherein the adjustment mechanism further includes a plurality of motors operable according to the adjustment parameters to actuate the plurality of linear actuators.

33. The virtual implant placement system of claim 29, further comprising an adjustable cut block, a docking station, and a locking mechanism, the adjustable cut block including a cut block base adjustably coupled to the guide surface, the docking station including at least one driving mechanism for adjusting a position of the guide surface relative to the cut block base according to the adjustment parameters when the adjustable cut block is mounted onto the docking station, the locking mechanism locking the position of the cut block base relative to the guide surface.

34. The virtual implant placement system of claim 33, wherein the driving mechanism is automatically actuated according to the adjustment parameters.

35. The virtual implant placement system of claim 23, wherein the processing device also determines a second cut plane adapted to resect the second bone, wherein the first cut plane and the second cut plane are determined independently so as to enable resectioning the first bone and the second bone in any order.

36. The virtual implant placement system of claim 23, further comprising a first support device including a first base having a first plurality of apertures configured to removably affix the first base to the first bone, and a first plurality of linear actuators rotatably coupling the first base and the first tracking assembly to move the first tracking assembly relative to the first bone.

37. The virtual implant placement system of claim 23, wherein the viewing device is positioned relative to the joint such that the joint and the virtual joint presented in the viewing device can be viewed simultaneously from a first direction.

38. The virtual implant placement system of claim 23, wherein the viewing device displays simultaneously the virtual joint and a visual representation of the joint.

* * * * *